(12) United States Patent
Jin et al.

(10) Patent No.: US 9,540,653 B2
(45) Date of Patent: Jan. 10, 2017

(54) LIGHT-INDUCIBLE PROMOTER AND GENE EXPRESSION SYSTEM CONTAINING SAME

(71) Applicant: INDUSTRY-UNIVERSITY COOPERATION FOUNDATION HANYANG UNIVERSITY, Seoul (KR)

(72) Inventors: Eon Seon Jin, Seoul (KR); Jae Hyeok Lee, Vancouver (CA); Seung Hye Park, Gyeonggi-do (KR); Kwang Ryul Baek, Gyeonggi-do (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 0 days.

(21) Appl. No.: 14/404,946

(22) PCT Filed: May 30, 2013

(86) PCT No.: PCT/KR2013/004762
§ 371 (c)(1),
(2) Date: Dec. 1, 2014

(87) PCT Pub. No.: WO2013/180488
PCT Pub. Date: Dec. 5, 2013

(65) Prior Publication Data
US 2015/0147782 A1    May 28, 2015

(30) Foreign Application Priority Data

Jun. 1, 2012 (KR) .................. 10-2012-0059411
Dec. 20, 2012 (KR) .................. 10-2012-0149832

(51) Int. Cl.
C12N 15/82 (2006.01)
C07K 14/405 (2006.01)
C12P 21/00 (2006.01)
C12P 21/02 (2006.01)

(52) U.S. Cl.
CPC ......... *C12N 15/8237* (2013.01); *C07K 14/405* (2013.01); *C12P 21/00* (2013.01); *C12P 21/02* (2013.01)

(58) Field of Classification Search
None
See application file for complete search history.

(56) References Cited

FOREIGN PATENT DOCUMENTS

EP       0310619 B1    4/1994
WO    WO 01-40492 A2    6/2001

OTHER PUBLICATIONS

International Search Report for PCT/KR2013/004762.
NCBr, GenBank acession No. A Y847686.1 (Jan. 1, 2006).
Shimizu-Sato, Sae et al., "A light-switchable gene promoter system", Naturebiotechno10gy, Oct. 2002, vol. 20, No. 10, pp. 1041-1044.
Balsalobre, Josefa M et al., "Light induction of gene expression in Myxococcus xanthus", PNAS, Apr. 1987, vol. 84, No. 8, pp. 2359-2362.

*Primary Examiner* — Addison D Ault
(74) *Attorney, Agent, or Firm* — Harness, Dickey & Pierce, P.L.C.

(57) ABSTRACT

The present invention relates to a light-inducible promoter and a gene expression system containing the same, and provides: a light-inducible promoter comprising a nucleotide sequence represented by SEQ ID NO: 12; and a method for producing heterologous proteins using the same. Since the light-inducible promoter of the present invention induces the expression of a gene by the irradiation of light and regulates an expression amount of the gene according to an intensity of light, it is possible to conveniently regulate the expression of the gene without straining the growth or metabolic process of an organism. In addition, the present invention can be applied to various types of organisms, and thus has a wide range of application.

10 Claims, 8 Drawing Sheets

Fig. 1a

```
1         10        20        30        40        50
|         |         |         |         |         |
CCCGGGCTGGTAAAATCCCATATGCATGCTAAACACAAGCTGGGCTATGC 50
TGACAGGAAGACAGGCTACTATACTTACTACCAGAGCTTGCTACCTCACG 100
TAAACAAGAAAATTAGCAATGCCTTTTGGAACATGCCCGGTCTCTCAACT 150
CGAATGAAACGCACTGTCTTCCAATACAGCACAGGCACCCTCTACAATCA 200
GAAACATGCGGTCCGATATAAAAGATCCACTAGCCTGACATGCCCCTAC 250
CTGATTGCCATCACATGGGTAGCGCTCTCCACATCCTATCTGGCTGCCAA 300
TGTCCTGTCATGCGTAACATGGTAACTGAACGTCACAATATCGCTTGCAG 350
GATGATTTTGAAACTGGTCAGTGAAGGCTCATATGGGCCAATCTTGTGC 400
                                 17LSIP →
AGTTGGATGCGGGCAACACAGACCGTTTGGCCCAGCACAACCTGCAAGTC 450
CCTGAGCAAGTCTCTAATCGTGCTGTACCTTCCAACCTCTTCAAACCCAC 500
GGTTTCGGTGCAATCCAGACGAAACTCCAGCCGCCCTGATGCAATCTTGG 550
TCACTCCTCACCCAACTAACCCAAACAGACCACCCACTTCACCCTCATAC 600
CGAGTACTGCGCAGTATGGGGAGTACCACAACTCCAGCCCGTCATATTCA 650
CTTGATAGAAATCAAATACTGCAAAGATACGAGGCCTGGTGCCCAGCTAG 700
AAGCCTCACAGCAACAACACAGTGAACTTTGCAAACAACTCCAAGGTGCA 750
GAGATCACTATCCACCCAATCCTCCTGGGTGTGGGTGGGACTATCTACAC 800
TGCCCATACCCTTGATCAATTAAAAAAAATAGGGATTGACTCACAGAGAT 850
CTGAAACACTTGCAAGAAAAATCCATGCCCATTCTGTACAATTTGCGCAC 900
AAACCTACCTCTACCAGACGTGCCATTGAAAATAAAAACACTCATCATGA 950
CACTGGTGCCCTGGAGCAGCGTGCTGCCAGAAACCCACCTGATCCACATT 1000
CACTCCCCTCTCATCTTCTGGTGGGGGAGACTCACGGCTCTTTGAGCCAA 1050
TGTGTCTCTCTTTCCTTAATTGATGTAGGGAGAGTTTTCTCTGCCCACAT 1100
AGTTTTTTCTCTTCTTTTTCTTTTCTAGCTCCTTACCTATTTGGTGGAAA 1150
GAGCTGAGACCTTTCGAAGCAATGAGTGTACGTAATATGGAATCATACCT 1200
TACAAAGGGAGCTAGAGGAACCAGTCGCCTATTGCCCATGCAGCATTAC 1250
                                 8LSIP →
CGCTGACTCAGCTCGACATATGGTGTTGGTAATTCAGCACAATTGGGCTC 1300
AACAAAGTTTTTGCTGTCAGTGAGAGGGCCGTAGACGTCTACACTCATAC 1350
ATACACACGTCGACAGGAGTGTAGATGGGAGTGTGTGTGTGTAAGTGTGT 1400
GCGTGCACGCGCGTATATGCATGTGTATATACGTGTTTGCGTATATATGT 1450
GTGTGTGTATGTGTGTGTTCATATGTATGTTGTTCATGCGTGCT 1500
GAGAACGCGTGTTCATGCACACCTGTAGCCTGTGCACCGTTAGCATTCTG 1550
GAAATGTCTTTTCCAGCCTCTGAGCACACCTCTTGGATCCTGTTGTGTCT 1600
GTGCCCCTGGATCCTTTATTACCCTCGAGGGTAGAGCTCTGGATCCCAG 1650
                                              4LSIP
```

Fig. 1b

```
TGTAGGTGTCTTTGCTAGTGTACTCCTACACGTCCTCAATGCACGAGCGT  1700
→
GCACACTAAACACTTGTGCATGCACTGTCACCAGGCTTTGGCAGCGCCAG  1750
GAGGTTCTTAAAGTGACATCCGTGTCCCGCAGCAACTTACATTGACCAAC  1800
                  ← GSP-2
AGTCAACACCCTCCAACCCTCACAGGTTCAAGACACATACAACACTGTTC  1850
ACTCACTCGTGATTTGCAAAATGTAAAGCCTTGGCCCTCTTGGCTTTTTT  1900
TTTCTCACGGGCAGCTCACCCACCGACTCACTCACGCACTCACCAACAGA  1950
GCGTGGCCTCGGAGCGTGAGGGCTCCGGGCCACACATTTGCCAGCCTGAA  2000
                                    1LSIP →
AACTTGCCAAAAACCACTCATCATCAAAACAACAAAAGCTTCAATCAAAA  2050
CTCGTTCCTACACCCACACGAACCGACCCGAACAATGCAGCTGCACATGA  2100
                 ← LSIP(reverse)
ACCTGTCCGCCTCCCGGATCGCGGCCGGTGCCATCAACGTGCGTCCCGCG  2150
CCCTTCGTACGTGGGGCTGCTACACCCAAGCGCACGAGCAGGCACATCGT  2200
GCGCGCCGAGAACGACCCCTCCACTCCCCCTCCCCCACAAGGATCGCAAG  2250
AGTCCCCCAGCTCCAGCCCTTCCCCACCTCCTCCTCCTCAGCCAACA     2300
GCCGCAGCTCCTACCGTGACAGGTGTGTAAAAGCTGGCCCCAGGAAGTTC  2350
CCCCTCTGCCAGGCTGGCTGGTTCTTGGGAGTAGTGTCTGCTGAACTTCT  2400
GCATGCAATGTGGTGCAAGCAACGACATGTWAACACACACACACACAC    2450
    ← GSP-1
ACACACACACACACACACACACACACACACACACGCGCGCGAGAGAGGGA  2500
ATGCGGGCACAGTCATGCAAGCAAACAAGCAGTGTGTGCTGCACCTGCAG  2550
CTCAGAGCATAAGAGCAGTGGCTGAGATCTGTTTTCTGTTGAGCACATTA  2600
AATTTGTTTGCAGCTCTGATGTGCACATCTATGCCAACTGCTGCTTATTT  2650
CTGATCATCAATATTTTGCCTGTCCGTTTTGGTGCA                2687
```

Fig. 2

Fig. 3
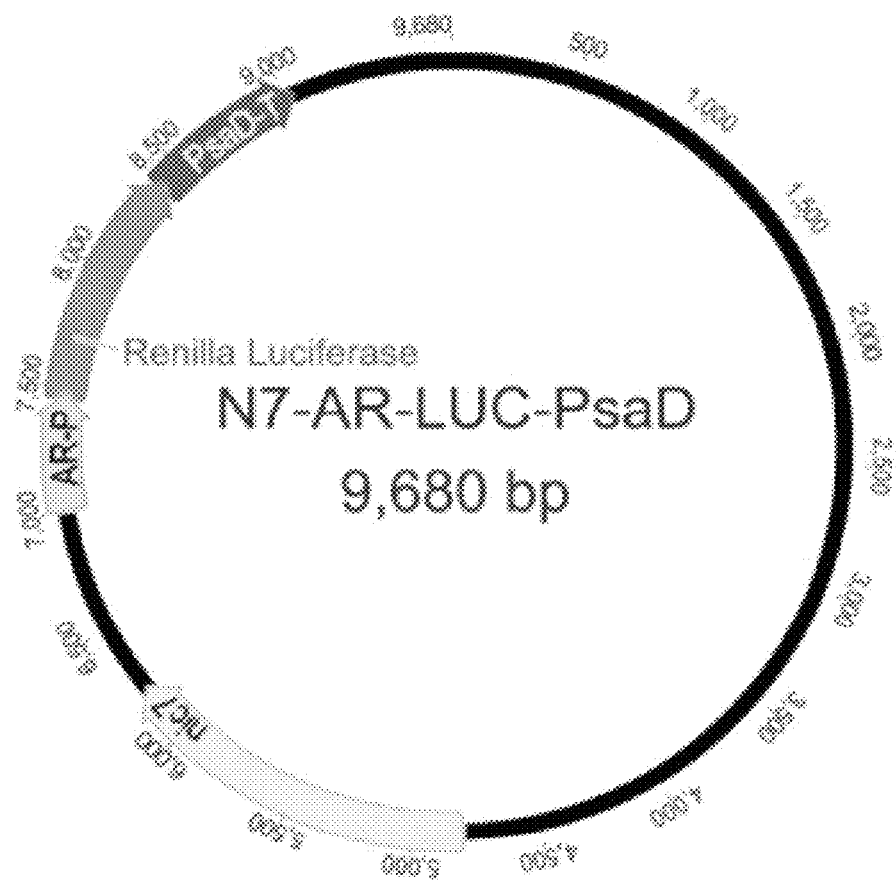
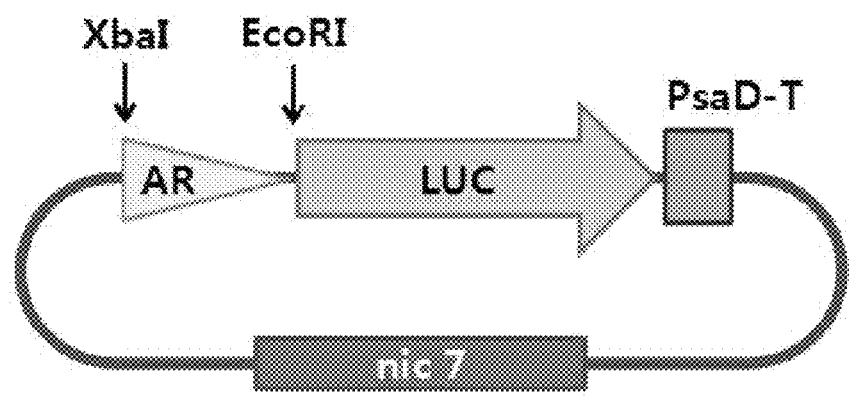

LIGHT-INDUCIBLE PROMOTER AND GENE EXPRESSION SYSTEM CONTAINING SAME

CROSS-REFERENCE TO RELATED APPLICATION AND CLAIM OF PRIORITY

This patent application is a National Phase application under 35 U.S.C. §371 of International Application No. PCT/KR2013/004762, filed 30 May 2013, which claims priority Korean Patent Application Nos. 10-2012-0059411 filed Jun. 1, 2012 and 10-2012-0149832 filed Dec. 20, 2012, in the Korean Intellectual Property Office, the disclosures of which are incorporated in their entirety by reference.

The present invention was made with the support of the Ministry of Education, Science, and Technology, of the Republic of Korea, under Project No. 2011-0031999, which was conducted in the research project titled "Big Science research and development programs (Korea CCS 2040 programs)" within the project named "Development of high-efficiency carbon dioxide fixation microalgae through molecular biological modification" by the Industry-Academic Cooperation Foundation, Hanyang University under the management of the Korea Carbon Capture & Sequestration R&D Center, from Nov. 11, 2011 to May 31, 2012.

BACKGROUND

Field of the Invention

The present invention relates to a novel promoter, and more particularly, to a light-inducible promoter and a gene expression system containing the same.

Background of Technique

In recent years, the efforts to analyze nucleotide sequences of genes are proceeding together with the attempts to use microalgae in the latest biotechnology including the development of biofuel, reduction in carbon dioxide generation, and production of high value-added materials. As part of these efforts, the attempts to introduce useful genes into existing microalgae to express desired traits have been continuing. However, microalgae have problems in view of the transgenic technology, such as low transformation efficiency and low expression efficiency of introduced genes (Lumbreras et al., Plnat J. 1998; 14: 441-447).

As one of the important schemes to solve the problems, various kinds of promoters for microalgae have been developed, and the use of promoters derived from the microalgae could induce effective transformation and gene expression when compared with the use of known promoters for higher plants (Walker et al., J. Applied Phycol. 2005; 17: 363-368). As a result, the promoters for *Chlamydomonas* (Schroda et al., The Plant Journal 2000; 21(2): 121-131) and *Dunaliella* (Li et al., Mol Biol. Rep. 2010; 37: 1143-1154) have been recently researched and presented.

The promoter derived from *Chlamydomonas* reported by Schroda et al. is prepared by fusing two different promoters, and induces gene expression mainly by thermal shock. In the case where the promoter is used, the application of heat for the introduction of gene expression may burden the growth or metabolic processes of algae.

The promoter derived from *Dunaliella* reported by Li et al. induces the expression of genes in the high salinity conditions (2M NaCl). Since the promoter can be applied to only halophilic species, the range of application thereof is narrow.

Therefore, the development of promoters which are applicable to various organisms and thus have a wide range of application, do not burden the growth or metabolic processes of organisms, and can conveniently regulate the expression of genes is urgent.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

SUMMARY

The present invention has been made in view of the above-mentioned problems, and an aspect of the present invention is to provide a promoter which is applicable to various kinds of organisms and can conveniently regulate the expression of a gene by the irradiation of light, and a gene expression system containing the same.

Other purposes and advantages of the present disclosure will become clarified by the following detailed description of the invention, claims, and drawings.

In accordance with an aspect of the present invention, there is provided a light-inducible promoter including a nucleotide sequence represented by SEQ ID NO: 12.

In accordance with another aspect of the present invention, there are provided an expression vector including the light-inducible promoter; and a transformant transformed with the expression vector.

In accordance with still another aspect of the present invention, there are provided an expression construct including a nucleotide sequence coding an exogenous protein and operably linked to a light-inducible promoter including a nucleotide sequence represented by SEQ ID NO: 12; an expression vector including the expression construct; and a transformant transformed with the expression vector.

In accordance with still another aspect of the present invention, there is provided a method for producing an exogenous protein, the method including: culturing the transformant; and irradiating light to the cultured transformant to produce the exogenous protein.

The light-inducible promoter of the present invention induces the expression of a gene by the irradiation of light and regulates the expression level of the gene according to the intensity of light, thereby conveniently regulating the expression of the gene without burdening the growth of microalgae or metabolic processes, and is applicable to various kinds of organisms and thus has a wide range of application.

Meanwhile, effects of the present invention are not limited to the above-mentioned effects, and other effects could be understood from the following descriptions by a person skilled in the art.

BRIEF DESCRIPTION OF THE DRAWINGS

FIGS. 1a and 1b show nucleotide sequencing results of the LSIP_P-cloned pGEM®-T easy vector (SEQ ID NO: 22) in examples <1-2> of the present invention:

Region indicated by the gray shade represents a first exon; and the other region excluding the region indicated by the gray shade represents the nucleotide sequence of LSIP_P.

Figure 2:
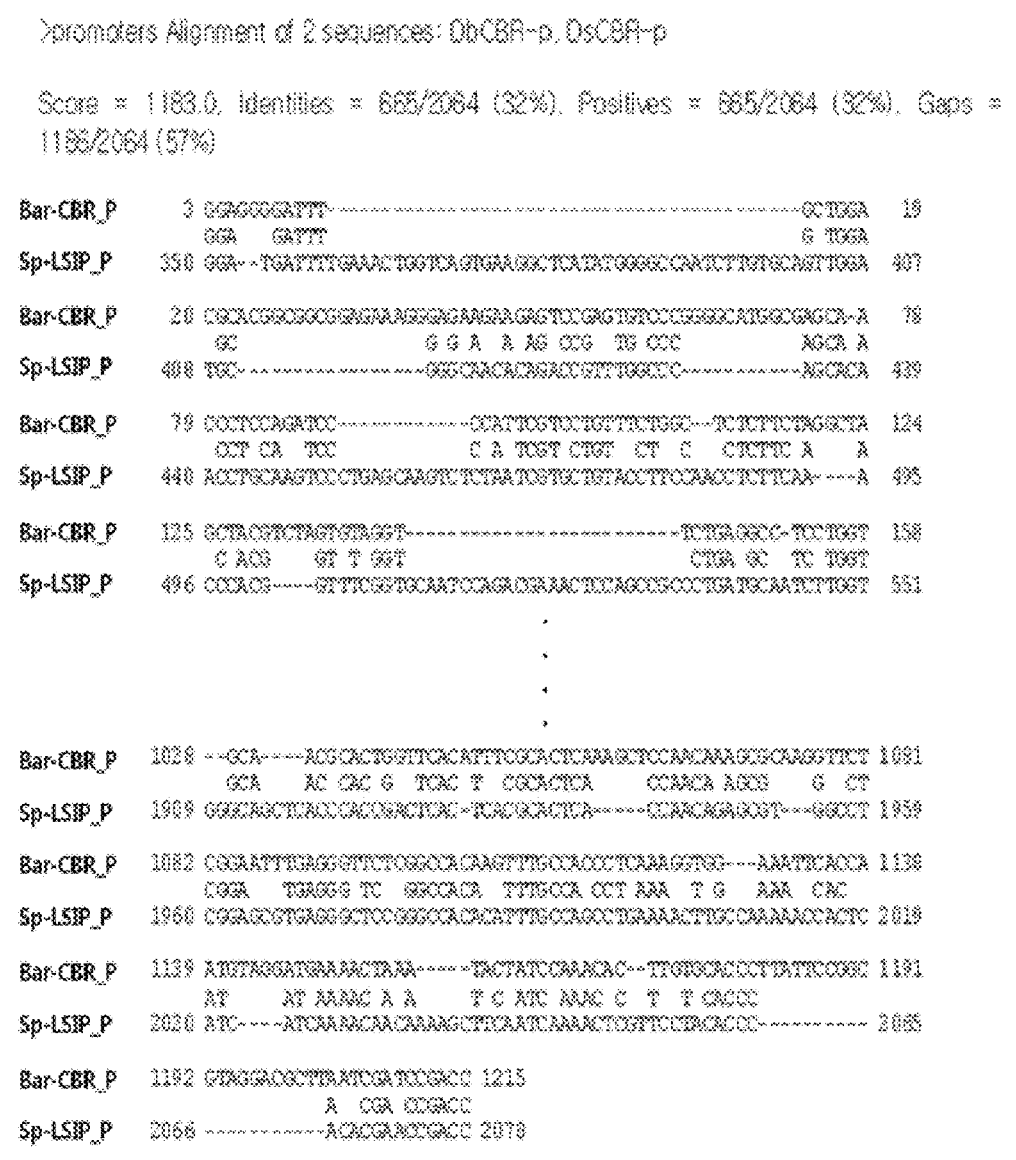

FIG. 2 illustrates a comparison of the nucleotide sequence between LSIP_P of *Donaliella* sp. (SEQ ID NO: 4) and cbr promoter of *Dunaliella bardawil* (SEQ ID NO: 15):

bar represents the nucleotide sequence of cbr promoter of *Dunaliella bardawil*; and sp represents the nucleotide sequence of LSIP_P of *Dunaliella* sp.

FIG. 3 shows a vector map of expression vector pN7-AR_P-LUC-TPsaD for *Chlamydomonas*:

nic7 represents a quinolinate synthetase gene used as a selectable marker at the time of transformation;

AR-P represents a recombinant promoter derived from *Chlamydomonas*;

*Renilla* luciferase CDS represents a gene coding an enzyme which degrades a substrate (Coelenterazine) to emit light; and PsaD-T represents a terminator region of PsaD gene derived from *Chlamydomonas*.

Figure 4:
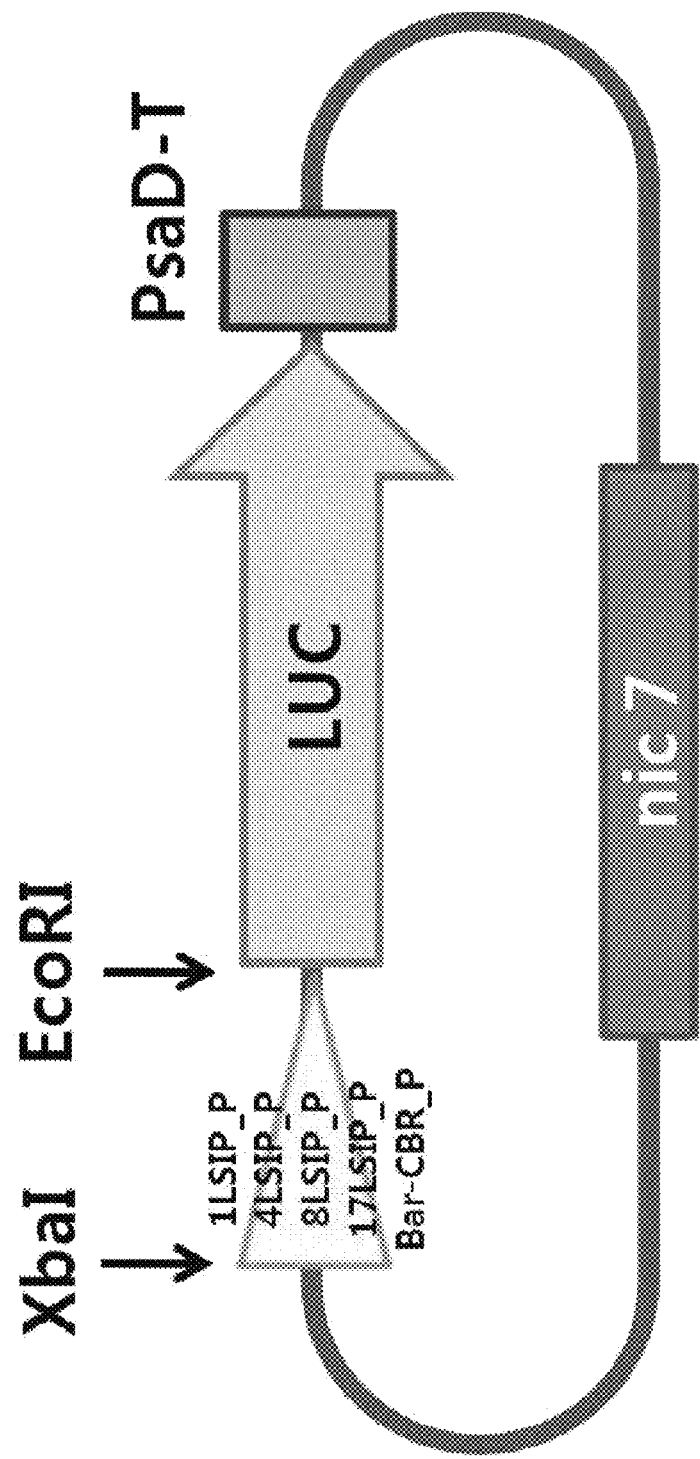

FIG. 4 shows a vector map of an expression vector obtained by inserting 1LSIP_P, 4LSIP_P, 8LSIP_P, 17LSIP_P or Bar-CBR_P at the AR_P removed site in pN7-AR_P-LUC-TPsaD of FIG. 3.

Figure 5:
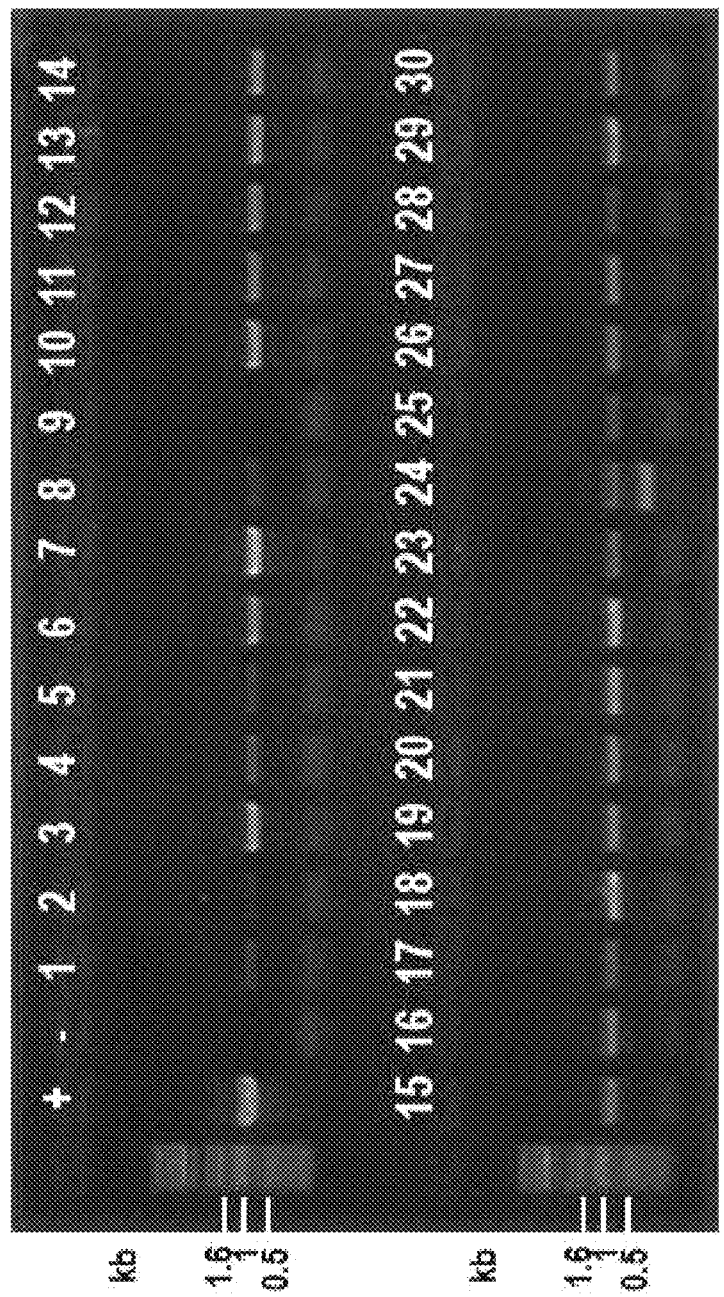

FIG. 5 is a gel image confirming whether pN7-1LSIP_P-LUC-TPsaD, pN7-4LSIP_P-LUC-TPsaD, pN7-8LSIP_P-LUC-TPsaD, pN7-17LSIP_P-LUC-TPsaD, and pN7-Bar-CBR_P-LUC-TPsaD were normally introduced by verifying the detection of bands corresponding to the 936-bp long luciferase gene via PCR of genomic DNAs isolated from transformants into which the above vectors are introduced:

signs + and − represent a plasmid vector used in the transformation and original untransformed *Chlamydomonas*, respectively; and numerals 1 to 6, 7 to 12, 13 to 18, 19 to 24, and 25 to 30 represent transformants into which 1LSIP_P, 4LSIP_P, 8LSIP_P, 17LSIP_P, and Bar-CBR_P are introduced before a reporter gene, respectively.

Figure 6:
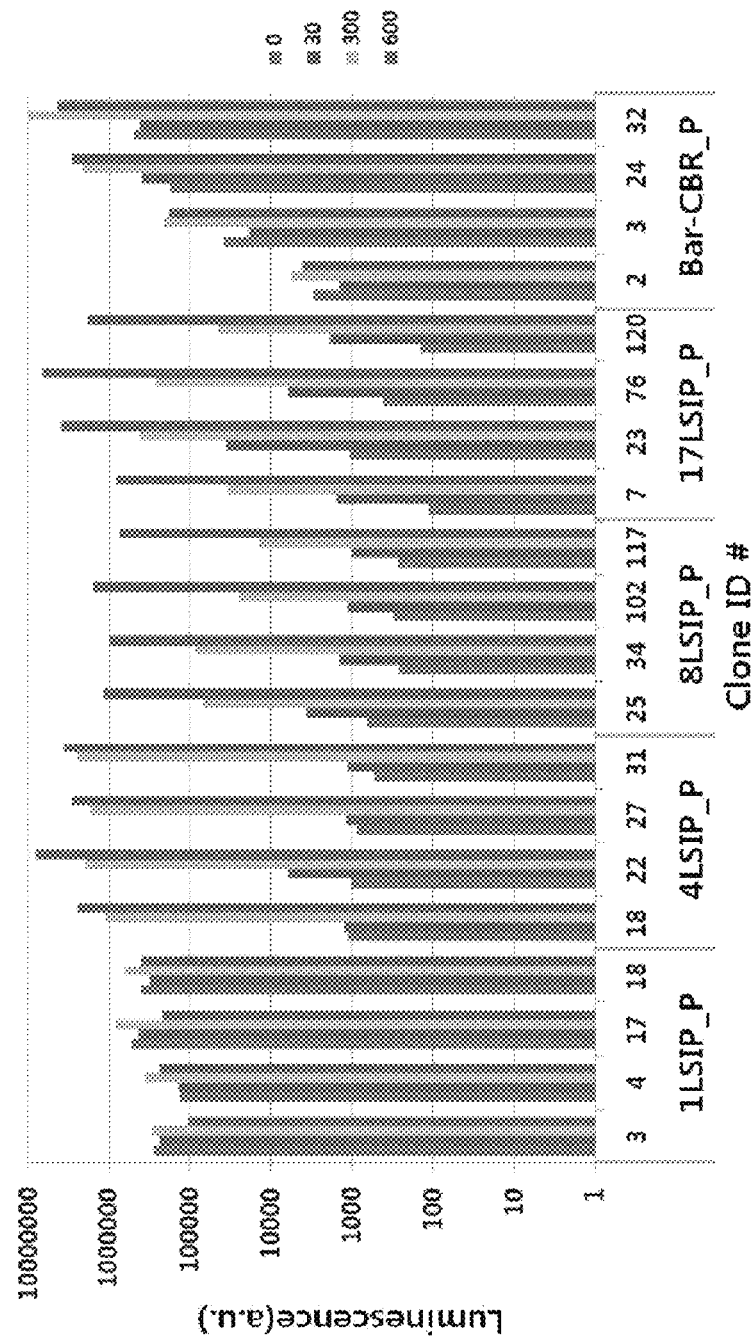

FIG. 6 is a graph showing the expression level of the luciferase regulated by 1LSIP_P, 4LSIP_P, 8LSIP_P, 17LSIP_P, and Bar-CBR_P according to the light intensity.

Figure 7:
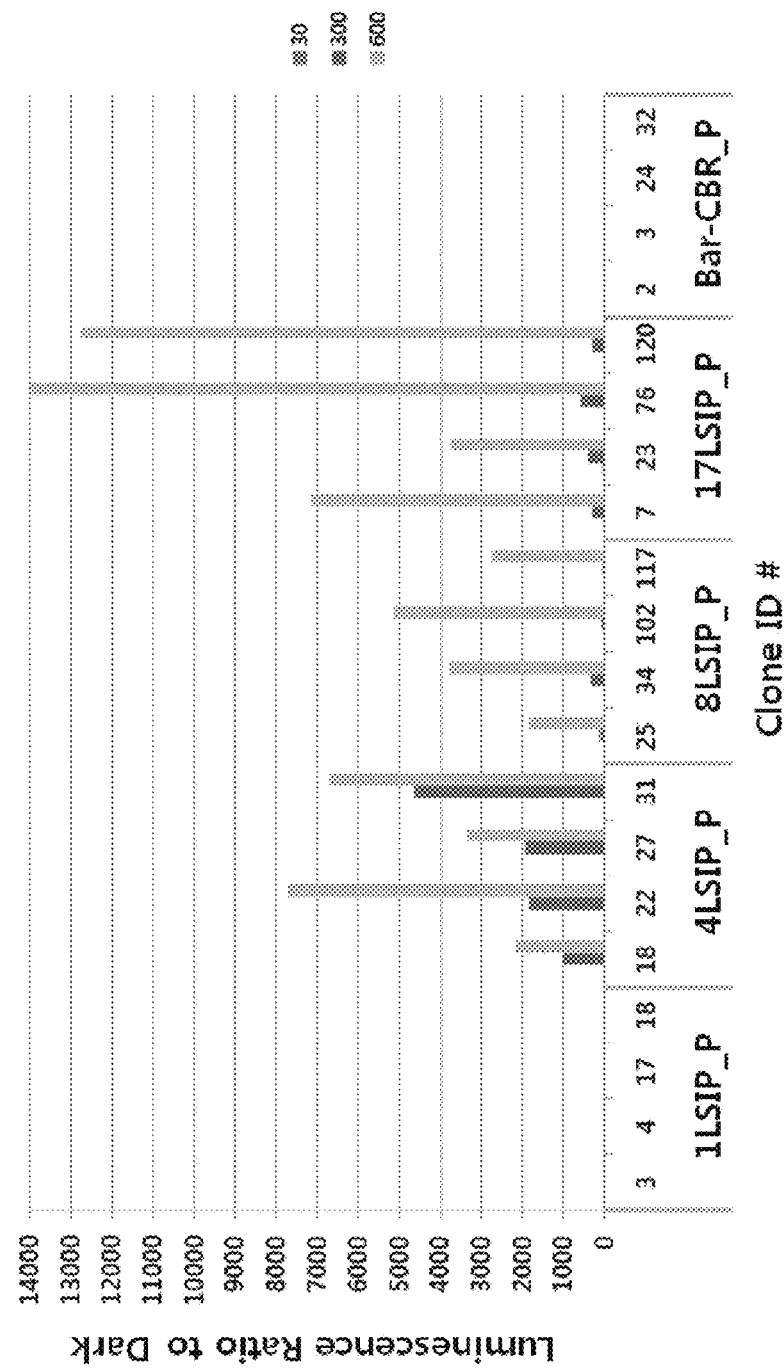

FIG. 7 is a graph showing the expression ratio of the luciferase regulated by LSIP_P, 4LSIP_P, 8LSIP_P, 17LSIP_P, and Bar-CBR_P according to the light intensity. Luminescence ratio represents (luminescence in cells exposed to light)/(luminescence in cells in the dark).

DETAILED DESCRIPTION

First, the terms used herein will be explained.

As used herein, the term "*Dunaliella* sp." refers to alga of *Dunaliella* that is newly renamed to be differentiated from typical *Dunaliella salina* shown in the document by Kim et al. (Phycological Research 2010; 58: 17-28), and *Dunaliella* sp. and *Dunaliella salina* are algae in the same genus but are different species.

As used herein, the term "light and salt inducible protein (LSIP)" refers to a protein having an amino acid sequence of SEQ ID NO: 3, derived from *Dunaliella* sp., and is known as carotenoid biosynthesis related protein (cbr protein) in the document by Kim et al. (Phycological Research 2010; 58: 17-28). In the document by Kim et al., the protein having the amino acid sequence of SEQ ID NO: 3 is named as cbr protein since it exhibits high identity (approximately 80%) with the cbr proteins of *Dunaliella salina* and *Dunaliella bardawil*, which are different species of the *Dunaliella*. However, unlike *D. salina* and *D. bardawil*, *Dunaliella* sp. does not accumulate carotenoid, and more particularly, the protein of SEQ ID NO: 3 derived from *Dunaliella* sp. needs to be differentiated from the cbr protein derived from *D. salina* and *D. bardawil*, in view of the fact that functions of the protein of SEQ ID NO: 3 in *Dunaliella* sp. or the correlation between the protein of SEQ ID NO: 3 and carotenoid has been never found. Herein, the protein of SEQ ID NO: 3 is renamed as light and salt inducible protein (LSIP), and defined to be differentiated from cbr protein of *D. salina* and *D. bardawil*.

As used herein, the term "promoter" refers to a DNA sequence regulating the expression of a gene which codes an exogenous protein and is operably linked to the promoter in a particular host cell.

As used herein, the term "expression vector" refers to a vector that can express a target exogenous protein in a host cell and includes necessary regulation factors that are operably linked so as to express the gene insert. Appropriate examples of the expression vector include a signal sequence for membrane targeting or secretion, or a leader sequence, as well as expression regulation sequences, such as a promoter, an operator, an initiation codon, a polyadenylation signal, and an enhancer, and can be variously prepared according to the purpose.

The vector system of the present invention can be constructed through various methods known in the art, and a specific method thereof is disclosed in Sambrook et al. *Molecular Cloning, A Laboratory Manual*, Cold Spring Harbor Laboratory Press (2001).

Hereinafter, the present invention will be described in detail.

1. *Dunaliella* sp. Derived Promoter

An aspect of the present invention provides a *Dunaliella* sp. derived promoter including a nucleotide sequence represented by SEQ ID NO: 18.

The *Dunaliella* sp. derived promoter of the present invention includes the nucleotide sequence of SEQ ID NO: 18.

The promoter includes a nucleotide sequence represented by SEQ ID NO: 18 having a length of 100 bp. The nucleotide sequence represented by SEQ ID NO: 18 induces and improves the "expression" of a gene coding an exogenous protein and operably linked to the downstream thereof, that is, the 3'-end of the nucleotide sequence. However, the nucleotide sequence of SEQ ID NO: 18 is merely a minimum unit of such a promoter that has properties of inducing and improving the expression of the gene, and thus the sequence of the promoter is not limited to the nucleotide sequence of SEQ ID NO: 18. Therefore, the promoter may be 100-bp to 2084-bp long nucleotide sequence selected to include the nucleotide sequence of SEQ ID NO: 18 in the nucleotide sequence of SEQ ID NO: 4. For example, the promoter may include a nucleotide sequence of SEQ ID NO: 12 having a length of 439 bp, a nucleotide sequence of SEQ ID NO: 1 having a length of 845 bp, or a nucleotide sequence of SEQ ID NO: 2 having a length of 1702 bp.

The promoter is derived from *Dunaliella* sp., and is preferably located at the upstream of a gene coding the LSIP protein of *Dunaliella* sp., but is not limited thereto. Therefore, the nucleotide sequence that is naturally derived or artificially synthesized may be as the promoter.

According to a specific embodiment of the present invention, the luciferase gene was operably linked to 1LSIP_P, which is a promoter including the nucleotide sequence of SEQ ID NO: 18, to construct the expression vector pN7-1LSIP_P-LUC-TPsaD having a map shown in FIG. 4, and the expression vector was introduced into cells of *Chlamydomonas reinhardtii* JL173, which is different genus and different species of *Dunaliella* sp. from which 1LSIP_P is derived, thereby constructing a transformant. Then, the transformant is dark-treated or exposed to the light having a light intensity of 30, 300, or 600 µmol photon/m²/s, thereby measuring the expression or non-expression of the luciferase, reporter gene, and the luminescence ratio. As a result, the luciferase, reporter gene, was expressed in only the transformants irradiated with light, regardless of the irradiation of light under 1SLIP_P and the light intensity (see table 3 and FIG. 6).

The above results showed that the nucleotide sequence represented by SEQ ID NO: 18 of the present invention is a basic unit having a promoter activity and can stably and very efficiently express an exogenous gene operably linked to the downstream of the nucleotide sequence represented by SEQ ID NO: 18.

2. Light-Inducible Promoter

Another aspect of the present invention provides a light-inducible promoter including a nucleotide sequence represented by SEQ ID NO: 12.

Still another aspect of the present invention provides an expression vector including the light-inducible promoter, and a transformant transformed with the expression vector.

The light-inducible promoter of the present invention includes the nucleotide sequence represented by SEQ ID NO: 12.

The promoter includes a nucleotide sequence represented by SEQ ID NO: 12 having a length of 439 bp. The nucleotide sequence of SEQ ID NO: 12 includes, a basic unit, the nucleotide sequence of SEQ ID NO: 18 having a promoter activity, and further includes a 339 bp-long nucleotide sequence, which is located at the 5' region of the nucleotide sequence represented by SEQ ID NO: 18 and can control the promoter activity of the nucleotide sequence of SEQ ID NO: 18 according to the light intensity.

The nucleotide sequence represented by SEQ ID NO: 12 induces the expression of a gene coding an exogenous protein and operably linked to the downstream thereof, that is, the 3'-end of the nucleotide sequence, and controls the expression level of the gene coding an exogenous protein according to the light intensity. However, the nucleotide sequence represented by SEQ ID NO: 12 is merely a minimum unit of such a promoter that has properties of regulating the expression of the gene linked to the downstream thereof according to the light intensity, and thus the sequence of the promoter is not limited to the nucleotide sequence of SEQ ID NO: 12. Therefore, the promoter may be 439-bp to 2084-bp long nucleotide sequence selected to include the nucleotide sequence of SEQ ID NO: 12 in the nucleotide sequence of SEQ ID NO: 4. For example, the promoter may be composed of a nucleotide sequence of SEQ ID NO: 1 having a length of 845 bp or a nucleotide sequence of SEQ ID NO: 2 having a length of 1702 bp.

The promoter is derived from *Dunaliella* sp., and is preferably located at the upstream of the gene coding the LSIP protein of *Dunaliella* sp., but is not limited thereto. Therefore, the nucleotide sequence which is naturally derived or artificially synthesized may be used as the promoter.

The light-inducible promoter is included in the expression vector, and can control the expression of the gene coding an exogenous protein and operably linked to the downstream thereof in a light intensity-dependent manner.

The expression vector may further include a multiple cloning site (MCS) for allowing the gene coding an exogenous protein to be operably inserted into the promoter. The gene coding an exogenous protein can be easily inserted into the expression vector by using the multiple cloning site.

The expression vector may further include a selectable marker for selecting host cells containing vectors. The selectable marker may be any kind of selectable marker known in the conventional art. An antibiotic resistant gene, a bioluminescent gene, a quinolinate synthetase gene, or the like may be used as the selectable marker, but the selectable marker is not limited thereto.

The expression vector may be one obtained by introducing the light-inducible promoter into any conventional expression vector, and may be a recombinant expression vector that is artificially designed by the known method. It would be easy for a person skilled in the art to which the prevention pertains to introduce the light-inducible promoter to construct an expression vector.

Any vector to which the light-inducible promoter can be introduced may be used as a vector for the construction of the expression vector, and examples thereof may include a plasmid vector, a cosmid vector, a bacteriophage vector, a viral vector, and the like. Particularly, it is preferable to use a vector that is stably present in host cells, such as microalgae or higher plants, and has a high copy number.

The expression vector is introduced into a host cell, and the host cell can be transformed with the expression vector.

The transformation may be easily conducted by a person skilled in the art using the known conventional transformation technique, and examples of the transformation technique may include transformation using glass beads described by Kindle (1990), protoplast transformation using calcium/polyethylene glycol, electroporation, microinjection, particle bombardment, eletrophoration, *Agrobacterium*-mediated transformation, transformation using a gene gun, physical induction, and the like. The transformation technique may be appropriately selected and performed by a person skilled in the art according to the kind and characteristics of host cell.

The host cells transformed with the expression vector are preferably microalgae or higher plants, and more preferably *Chlamydomonas* or *Dunaliella*, but are not limited thereto. Thus, any cell that has a RNA polymerase capable of recognizing the promoter of the present invention may be used.

In a specific embodiment of the present invention, the expression vectors pN7-4LSIP_P-LUC-TPsaD, pN7-8LSIP_P-LUC-TPsaD, and pN7-17LSIP_P-LUC-TPsaD having a map shown in FIG. 4 were constructed by operably linking the luciferase gene to 4LSIP_P, which is a promoter including the nucleotide sequence of SEQ ID NO: 12, 8LSIP_P, which is a promoter including the nucleotide sequence of SEQ ID NO: 1, and 17LSIP_P, which is a promoter including the nucleotide sequence of SEQ ID NO: 2, respectively. Then, the three expression vectors pN7-4LSIP_P-LUC-TPsaD, pN7-8LSIP_P-LUC-TPsaD, and pN7-17LSIP_P-LUC-TPsaD were introduced into cells of *Chlamydomonas reinhardtii* JL173, which is a different genus and different species of *Dunaliella* sp. from which 1LSIP_P was derived, thereby constructing transformants, respectively. Then, the transformants were dark-treated or exposed to the light having a light intensity of 30, 300, or 600 µmol photon/m²/s, thereby measuring the expression or non-expression of the luciferase reporter gene and the luminescence ratio. The results confirmed that the luciferase reporter gene was expressed in only the transformants irradiated with light, and the higher the light intensity, the higher the luminescence ratio (see table 3 and FIG. 6).

The above results showed that the nucleotide sequence represented by SEQ ID NO: 12 and the nucleotide sequence represented by SEQ ID NO: 1 or 2 including the nucleotide sequence represented by SEQ ID NO: 12 exhibited activity of the light-inducible promoter. That is, it can be seen that the nucleotide sequence represented by SEQ ID NO: 12 functions as a minimum unit having activity of the light-inducible promoter, and the nucleotide sequences selected to include the nucleotide sequence of SEQ ID NO: 12 and having various lengths also had activity of the light-inducible promoter. In addition, it was confirmed that LSIP_P can regulate the gene coding an exogenous protein in a light-dependent manner even in microorganisms that are not algae belonging to *Dunaliella* and are different genus and different species of *Dunaliella*, and thus can be widely applied to various species of microorganisms.

3. Production of Exogenous Protein Using Light-Inducible Promoter

Still another aspect of the present invention provides: an expression construct having a nucleotide sequence coding an exogenous protein and operably linked to a light-inducible promoter including a nucleotide sequence represented by SEQ ID NO: 12; an expression vector including the expression construct; and a transformant transformed with the expression vector.

Still another aspect of the present invention provides a method for producing an exogenous protein, the method including: culturing the transformant; and irradiating light to the cultured transformant.

The expression construct of the present invention includes a light-inducible promoter including a nucleotide sequence represented by SEQ ID NO: 1 and a gene coding an exogenous protein and operably linked to the light-inducible promoter.

The light-inducible promoter is as described in section "2. Light-inducible promoter" above, and thus, detailed descriptions of the light-inducible promoter will be omitted by referring to the description of section "2. Light-inducible promoter" and hereinafter, only specific features of the expression construct will be described.

The exogenous protein means a protein to be produced, and may be any kind of protein of which the nucleotide sequence of a gene is known. In particular, the exogenous protein includes hormones, hormone analogues, enzymes, enzyme inhibitors, signaling proteins or fragments thereof, antibodies or fragments thereof, single chain antibodies, affibodies, peptide aptamers, binding proteins or binding domains thereof, antigens, adhesion proteins, structural proteins, regulatory proteins, toxin proteins, cytokines, transcription factors, and blood coagulation factors, but is not limited thereto.

The gene coding an exogenous protein is operably linked to the light-inducible promoter. The term "operably linked" refers to the linkage in such a manner that the expression of the exogenous protein can be regulated by activity of the light-inducible promoter. Thus, the expression construct formed by operably linking the gene coding an exogenous protein to the light-inducible promoter is an expression cassette functioning as a unit for expressing a gene coding the exogenous protein.

According to an embodiment of the present invention, the expression construct of the present invention further includes a terminate sequence located at the downstream of the nucleotide sequence coding an exogenous protein. The terminate sequence (that is, poly A signal sequence) useable herein includes various terminate sequences operable in algae known in the art, and examples thereof include PsaD-T (terminator of PsaD gene derived from *Chlamydomonas*).

The expression construct is included in the expression vector, and can control the expression of the gene coding an exogenous protein in a light-dependent manner.

According to an embodiment of the present invention, examples of the transformant including the expression vector are algae, and specifically, green algae, e.g., green algae, such as *Dunaliella* and *Chlamydomonas*.

In addition, the expression vector including the expression vector is introduced into a host cell, and the host cell can be transformed with the expression vector. The transformant formed as above may be used in the production of the exogenous protein.

The method for producing an exogenous protein of the present invention includes: 1) culturing the transformant; and irradiating light to the cultured transformant.

The culturing in step 1) may be appropriately performed by a person skilled in the art while the culturing method, culturing medium, and culturing condition are differentiated according to the kind and characteristics of the transformant.

The irradiating of the light in step 2) is performed to induce the expression of the gene coding an exogenous protein in the transformant cultured in step 1), and the expression of the gene is regulated by activity of the light-inducible promoter.

In step 2), the intensity of the light may be appropriately selected according to the production standard of the exogenous protein by a person skilled in the art, and the intensity of the irradiation light may be 10 to 1000 µmol photon/m$^2$/s, but is not limited thereto. In addition, in step 2), the irradiation time of the light may be appropriately selected according to the production standard of the exogenous protein by a person skilled in the art, for example, the irradiation time of the light may be 1 to 5 hours, but is not limited thereto.

The method for producing an exogenous protein may further include isolating the expressed exogenous protein from the transformant.

The exogenous protein can be easily produced by using the expression construct, the expression vector including the expression construct, and the transformant including the expression vector.

EXAMPLES

Hereinafter, the present invention will be described in detail with reference to the following examples.

However, the following examples are merely for illustrating the present invention, and thus are not intended to limit the scope of the present invention.

Example 1

Cloning of Light-Inducible Promoter LSIP_P and Nucleotide Sequencing

With reference to documents by Park et al. (Marine Biotechnology, 2006; 8: 120-128) and Kim et al. (Phycological Research 2010; 58: 17-28), the upstream region of LSIP, of which the expression level is known to be changed according to the light intensity, was cloned from *Dunaliella* sp., sequenced, and named as LSIP_P.

<1-1> Cloning of Light-Inducible Promoter LSIP_P

The light-inducible promoter LSIP_P from the genomic DNA of *Dunaliella* sp. established in the documents by Park et al. (Marine Biotechnology, 2006; 8: 120-128) and Kim et al. (Phycological Research 2010; 58: 17-28) was cloned into the pGEM®-T easy vector (Promega, USA) using GenomeWalker™ Universal Kit (Cat. #638904) (Clontech, USA) according to the protocol provided by the manufacturer thereof, thereby constructing pGEM®-T-LSIP_P. In the cloning procedure of LSIP_P using the Kit, the nucleotide sequence represented by SEQ ID NO: 6 and the nucleotide sequence represented by SEQ ID NO: 7 were used as gene specific primer 1 (GSP1) and gene specific primer 2 (GSP2), respectively.

<1-2> Nucleotide Sequencing of Light-Inducible Promoter LSIP_P

The LSIP_P promoter cloned in example <1-1> was subjected to nucleotide sequencing by Macrogen, Korea. For the nucleotide sequencing, GSP1 of SEQ ID NO: 6, GSP2 of SEQ ID NO: 7, and an adaptor primer provided in the GenomeWalker™ Universal Kit were used.

The results confirmed that the nucleotide sequence represented by SEQ ID NO: 5 was cloned in the pGEM®-T easy vector (FIGS. 1a and 1b). It was confirmed from the above nucleotide sequencing results that the nucleotide sequence located at the upstream of the first exon sequence of LSIP in the nucleotide sequence represented by SEQ ID NO: 5 was the nucleotide sequence of LSIP_P, and resultantly, LSIP_P had the nucleotide sequence represented by SEQ ID NO: 4.

<1-3> Homology Analysis of Light-Inducible Promoter LSIP_P

The homology analysis between the nucleotide sequence of LSIP_P obtained in example <1-2> and the nucleotide sequence (SEQ ID NO: 4) of the cbr promoter derived from *Dunaliella bardawil* found in the document by Lers et al. (The Journal of Biological Chemistry 1991; 266(21): 13598-13705) was conducted through comparison therebetween.

The results confirmed that the homology between LSIP_P of the present invention and the cbr promoter of *D. bardawil* was very low, 32% (FIG. 2).

Example 2

Construction of Expression Vector Including LSIP_P

In order to verify effects of LSIP_P cloned in example 1 and applicability of LSIP_P to microorganisms of different genus and different species, an expression system of *Chlamydomonas reinhardtii*, which is not an alga of *Dunaliella* but a microorganism of another genus.

In order to use the expression system of *C. reinhardtii*, pN7-AR_P-LUC-TPsaD, which is an expression vector for *Chlamydomonas* developed by the present inventors, was used. The vector pN7-AR_P-LUC-TPsaD has a nucleotide sequence of SEQ ID NO: 8, and the map of the vector is shown in FIG. 3.

<2-1> Cloning pN7-1LSIP_P-LUC-TPsaD

Polymerase chain reaction (PCT) was conducted by using pGEM®-T-LSIP_P prepared in example 1 as a template and a primer pair composed of a primer of SEQ ID NO: 19 having the XbaI restriction enzyme site and a primer of SEQ ID NO: 11 having the EcoRI restriction enzyme site, thereby obtaining 1LSIP_P having a nucleotide sequence of SEQ ID NO: 18.

Then, AR_P was removed from pN7-AR_P-LUC-TPsaD using the restriction enzymes XbaI and EcoRI, and replaced with the obtained 1LSIP_P, thereby constructing the expression vector pN7-1LSIP_P-LUC-TPsaD having a map shown in FIG. 4.

<2-2> Cloning pN7-4LSIP_P-LUC-TPsaD

Polymerase chain reaction (PCT) was conducted by using pGEM®-T-LSIP_P prepared in example 1 as a template and a primer pair composed of a primer of SEQ ID NO: 13 having the XbaI restriction enzyme site and a primer of SEQ ID NO: 11 having the EcoRI restriction enzyme site, thereby obtaining 4LSIP_P having a nucleotide sequence of SEQ ID NO: 12.

Then, AR_P was removed from pN7-AR_P-LUC-TPsaD using the restriction enzymes XbaI and EcoRI, and replaced with the obtained 4LSIP_P, thereby constructing the expression vector pN7-4LSIP_P-LUC-TPsaD having a map shown in FIG. 4.

<2-3> Cloning pN7-8LSIP_P-LUC-TPsaD

Polymerase chain reaction (PCT) was conducted by using pGEM®-T-LSIP_P prepared in example 1 as a template and a primer pair composed of a primer of SEQ ID NO: 9 having the XbaI restriction enzyme site and a primer of SEQ ID NO: 11 having the EcoRI restriction enzyme site, thereby obtaining 8LSIP_P having a nucleotide sequence of SEQ ID NO: 1.

Then, AR_P was removed from pN7-AR_P-LUC-TPsaD using the restriction enzymes XbaI and EcoRI, and replaced with the obtained 8LSIP_P, thereby constructing the expression vector pN7-8LSIP_P-LUC-TPsaD having a map shown in FIG. 4.

<2-4> Cloning pN7-17LSIP_P-LUC-TPsaD

Polymerase chain reaction (PCT) was conducted by using pGEM®-T-LSIP_P prepared in example 1 as a template and a primer pair composed of a primer of SEQ ID NO: 10 having the XbaI restriction enzyme site and a primer of SEQ ID NO: 11 having the EcoRI restriction enzyme site, thereby obtaining 17LSIP_P having a nucleotide sequence of SEQ ID NO: 2.

Then, AR_P was removed from pN7-AR_P-LUC-TPsaD using the restriction enzymes XbaI and EcoRI, and replaced with the obtained 17LSIP_P, thereby constructing the expression vector pN7-17LSIP_P-LUC-TPsaD having a map shown in FIG. 4.

Example 3

Transformation of *Chlamydomonas reinhardtii*

<3-1> Preparation of Gamete Autolysine

In the procedure of transforming *C. reinhardtii* with the expression vectors pN7-1LSIP_P-LUC-TPsaD, pN7-4LSIP_P-LUC-TPsaD, pN7-SLSIP_P-LUC-TPsaD, and pN7-17LSIP_P-LUC-TPsaD, which were prepared in example 2, the gamete autolysine used to removed the cell wall of *C. reinhardtii* was prepared by the method established in the document by Harris et al. (*Chlamydomonas* Handbook (Academic, New York), 00.47, 593-594). For the preparation of gamete autolysine, wild type *Chlamydomonas reinhardtii* CC620 and *Chlamydomonas reinhardtii* CC621, which have good mating efficiency therebetween, were used. Specifically, *C. reinhardtii* CC620 and *C. reinhardtii* CC621 cells, which were respectively cultured in TAP liquid media having a composition shown in table 1 below, were plated on TAP solid media at a cell density of about 1×10$^6$ cell/plate, and cultured for one week. Then, the cultured cells were suspended in TAP liquid media without a nitrogen source, and cultured for 5 hours. Then, the *C. reinhardtii* CC620 and *C. reinhardtii* CC621 cells were respectively counted, and two *C. reinhardtii* CC620 and *C. reinhardtii* CC621 cells were mixed at a cell count ratio of 1:1, and then cultured for 15 minutes. The mixed and cultured *C. reinhardtii* CC620 and *C. reinhardtii* CC621 cells were centrifuged to obtain supernatants, and the obtained supernatants were filtered using a 0.45 μm syringe filter, thereby preparing gamete autolysine. The prepared gamete autolysine was stored at −80 to −70° C.

TABLE 1

| Component | Concentration |
|---|---|
| TRIS | 2.42 g/L |
| NH$_4$Cl | 0.4 g/L |
| CaCl$_2$•2H$_2$O | 0.05 g/L |
| MgSO$_4$•7H$_2$O | 0.1 g/L |
| K$_2$HPO$_4$ | 54 mg/L |
| KH$_2$PO$_4$ | 27 mg/L |
| Na$_2$EDTA•2H$_2$O | 50 mg/L |
| FeSO$_4$•7H$_2$O | 5 mg/L |
| ZnSO$_4$•7H$_2$O | 22 mg/L |
| H$_3$BO$_3$ | 11.4 mg/L |
| MnCl$_2$•4H$_2$O | 5.2 mg/L |
| CuCl$_2$•2H$_2$O | 1.1 mg/L |
| Na$_2$MoO$_4$•2H$_2$O | 2.6 mg/L |
| CoCl$_2$•6H$_2$O | 1.6 mg/L |
| acetic acid | 1 mL/L |
| pH 7.2 | |

<3-2> Introduction of pN7-1LSIP_P-LUC-TPsaD, pN7-4LSIP_P-LUC-TPsaD, pN7-8LSIP_P-LUC-TPsaD, and pN7-17LSIP_P-LUC-TPsaD, and Selection of Transformants The expression vectors pN7-1LSIP_P-LUC-TPsaD, pN7-4LSIP_P-LUC-TPsaD, pN7-8LSIP_P-LUC-TPsaD, and pN7-17LSIP_P-LUC-TPsaD prepared in example 2 were introduced into *Chlamydomonas reinhardtii* JL173 cells, according to the method established in the document by Kindle et al. (Proc. Natl Acad. Sci. USA 1990; 87: 1228-1232). Specifically, the *C. reinhardtii* JL173 cells cultured until the log-growth phase were harvested by centrifugation, and resuspended in the gamete autolysine prepared in example <3-1>, followed by reaction at room temperature for 60 minutes. The *C. reinhardtii* JL173 cells reacted with the gamete autolysine as above were harvested by centrifugation, and resuspended in TAP liquid medium to adjust the cell density to 1×10$^8$ to 3×10$^8$ cell/ml. A 0.3-mL aliquot of the cell suspension was transferred to test tubes containing 0.3 g of glass beads with a diameter of 425 to 600 μm (G8772; Sigma, USA). In each of the tubes, 5 μl of each of the vectors of example 2, which was cut using 1 μg of Kpnl to be linearized, and 100 μl of 20% polyethylene glycol (PEG) 8000 were added, and then the mixture was agitated by vortexing for 25 seconds. Subsequently, TAP medium was further added, and then centrifugation was performed, thereby harvesting cells. The harvested cells were resuspended in 10 ml of TAP liquid medium, followed by centrifugation, thereby re-harvesting cells. The re-harvested cells were resuspended in 0.3 ml of TAP liquid medium. Then, the resuspended cells were added to TAP medium mixed with 0.5% of agarose, which was heated and cooled to 45° C., and then well agitated. Then, the cells are plated and solidified onto TAP solid medium mixed with 1 ppm of 3-acetylpyridine (Aldrich, USA), and then cultured for 5 to 7 days.

When the cells cultured for 5 to 7 days start to form green colonies, the colonies were transferred to TAP sodium medium using toothpicks, thereby selecting *C. reinhardtii* JL173 transformants normally transformed with the expression vectors pN7-1LSIP_P-LUC-TPsaD, pN7-4LSIP_P-LUC-TPsaD, pN7-8LSIP_P-LUC-TPsaD, and pN7-17LSIP_P-LUC-TPsaD.

<3-3> Verification of Introduction of pN7-1LSIP_P-LUC-TPsaD, pN7-4LSIP_P-LUC-TPsaD, pN7-8LSIP_P-LUC-TPsaD, and pN7-17LSIP_P-LUC-TPsaD The pN7-1LSIP_P-LUC-TPsaD-normally introduced transformant, the pN7-4LSIP_P-LUC-TPsaD-normally introduced transformant, the pN7-8LSIP_P-LUC-TPsaD-normally introduced transformant, and the pN7-17LSIP_P-LUC-TPsaD-normally introduced transformant, which were selected in example <3-2>, were cultured in TAP liquid media until approximately the log-growth phase, and then harvested. Then, genomic DNAs were isolated from the transformants using the DNeasy plant mini kit (69104; QIAGEN, USA) according to the protocol provided by the manufacturer.

PCR using a pair of primers of SEQ ID NO: 20 and SEQ ID NO: was conducted by using, as templates, the genomic DNAs isolated from the pN7-1LSIP_P-LUC-TPsaD-normally introduced transformant, the pN7-4LSIP_P-LUC-TPsaD-normally introduced transformant, the pN7-8LSIP_P-LUC-TPsaD-normally introduced transformant, and the pN7-17LSIP_P-LUC-TPsaD-normally introduced transformant, to verify whether the 936-bp long luciferase gene was introduced.

The results confirmed that the bands corresponding to the 936-bp long luciferase gene were detected in the genomic DNAs, respectively, (lane 1 to 24 in FIG. 5), and the above results confirmed that four kinds of vectors pN7-1LSIP_P-LUC-TPsaD, pN7-4LSIP_P-LUC-TPsaD, pN7-8LSIP_P-LUC-TPsaD, and pN7-17LSIP_P-LUC-TPsaD were normally introduced into *C. reinhardtii* JL173 cells.

Example 4

Measurement of LSIP_P Activity

While the pN7-1LSIP_P-LUC-TPsaD transformant, pN7-4LSIP_P-LUC-TPsaD transformant, pN7-8LSIP_P-LUC-TPsaD transformant, and pN7-17LSIP_P-LUC-TPsaD transformant, which were selected in example <3-2>, were divisionally cultured in several test tubes containing TAP liquid medium, the test tubes were dark-treated or exposed to light of 30, 300, or 600 μmol photon/m$^2$/s for 3 hours. Then, the transformants were harvested, and the luciferase luminescence was measured through Luminometer (Glo-Max™ 20/20; Promega, USA) using the *Renilla* Luciferase assay kit (E2810; Promega, USA) according to the protocol provided by the manufacturer. In order to analyze the level of the luciferase expression for each light intensity, the luminescence ratio, which was calculated by dividing the luminescence of the transformant irradiated with light of 0, 30, 300, or 600 μmol photon/m$^2$/s by the luminescence of the dark-treated transformant, was compared.

As a result, the luciferase reporter gene exhibited high luminescence regardless of the intensity of the light irradiated to the downstream of 1LSIP_P. In addition, as the intensity of the light irradiated to the downstream of each of 4LSIP_P, 8LSIP_P, and 17LSIP_P increased, the luciferase reporter gene exhibited higher luminescence, and the luminescence ratio for light of strong intensity (300 or 600 μmol photon/m$^2$/s) over light of weak intensity (0 or 30 μmol photon/m$^2$/s) was exhibited to be large (table 2 and FIGS. 6 and 7). It can be seen from the above results that 1LSIP_P having the nucleotide sequence of SEQ ID NO: 18 is a basic unit for allowing LSIP_P of the present invention to have a promoter activity. Thus, it can be seen that LSIP_P of the present invention, such as 4LSIP_P, 8LSIP_P, or 17LSIP_P in which a partial nucleotide sequence is added to the 5' end of 1LSIP_P, can regulate the expression of the gene linked to the downstream thereof in a light intensity-dependent manner.

TABLE 2

| Clone | | Luminescence | | | | Luminescence ratio (light/dark) | | |
|---|---|---|---|---|---|---|---|---|
| | | Light intensity (μmol photons/m²/s) | | | | | | |
| | ID | 0 | 30 | 300 | 600 | 30 | 300 | 600 |
| 1LSIP_P | 3 | 283639 | 238069 | 300044 | 108731 | 0.84 | 1.06 | 0.38 |
| | 4 | 135213 | 141029 | 356974 | 236853 | 1.04 | 2.64 | 1.75 |
| | 17 | 520749 | 435440 | 819162 | 220960 | 0.84 | 1.57 | 0.42 |
| | 18 | 397822 | 311136 | 640419 | 406800 | 0.78 | 1.61 | 1.02 |
| 4LSIP_P | 18 | 1151 | 1231 | 1145962 | 2485491 | 1.07 | 995.62 | 2159.41 |
| | 22 | 1028 | 6075 | 1881269 | 7930784 | 5.91 | 1830.92 | 7718.52 |
| | 27 | 866 | 1185 | 1693262 | 2923951 | 1.37 | 1956.40 | 3378.34 |
| | 31 | 545 | 1163 | 2529379 | 3658318 | 2.13 | 4641.06 | 6712.51 |
| 8LSIP_P | 25 | 641 | 3700 | 67514 | 1177278 | 6 | 105 | 1837 |
| | 34 | 262 | 1424 | 86388 | 994563 | 5 | 330 | 3796 |
| | 102 | 306 | 1127 | 24174 | 1570141 | 4 | 79 | 5131 |
| | 117 | 270 | 989 | 13905 | 744517 | 4 | 52 | 2757 |
| 17LSIP_P | 7 | 112 | 1552 | 34841 | 799686 | 14 | 311 | 7140 |
| | 23 | 1045 | 35776 | 420050 | 3923813 | 34 | 402 | 3755 |
| | 76 | 407 | 6144 | 267140 | 6639544 | 13 | 568 | 14127 |
| | 120 | 142 | 1848 | 44330 | 1811656 | 13 | 312 | 12758 |

Example 5

Activity Comparison with Cbr Promoter Derived from *Dunaliella bardawil*

Between the LSIP promoter derived from *Dunaliella* sp. of the present invention and the cbr promoter derived from *Dunaliella bardawil* found in the document by Lers et al. (The Journal of Biological Chemistry 1991; 266(21): 13598-13705), the inducibility of the promoter activity by light was compared.

Polymerase chain reaction (PCT) was conducted by using the genomic DNA of *Dunaliella bardawil* established in the document by Lers et al. as a template gene, and a primer pair composed of a primer of SEQ ID NO: 16 having the XbaI restriction enzyme site and a primer of SEQ ID NO: 17 having the EcoRI restriction enzyme site, thereby obtaining Bar-CBR_P having a nucleotide sequence of SEQ ID NO: 14.

Then, AR_P was removed from pN7-AR_P-LUC-TPsaD using the restriction enzymes XbaI and EcoRI by the same method as in example 2, and replaced with the obtained Bar-CBR_P, thereby constructing the expression vector pN7-Bar-CBR_P-LUC-TPsaD having a map shown in FIG. 4.

The normal introduction of pN7-Bar-CBR_P-LUC-TPsaD into *C. reinhardtii* JL173 cells was verified by transforming *C. reinhardtii* with the prepared expression vector pN7-Bar-CBR_P-LUC-TPsaD by the same method as in example 3, selecting normally transformed transformants, and conducting PCR using the pN7-Bar-CBR_P-LUC-TPsaD genomic DNA isolated from the transformants as a template, and a primer pair composed of a primer of SEQ ID NO: 20 and a primer of SEQ ID NO: 21 to confirm bands corresponding to the 936-bp long luciferase gene (lane 25 to lane 30 in FIG. 5).

While the pN7-Bar-CBR_P-LUC-TPsaD transformant selected above, and the pN7-1LSIP_P-LUC-TPsaD transformant, pN7-4LSIP_P-LUC-TPsaD transformant, pN7-8LSIP_P-LUC-TPsaD transformant, and pN7-17LSIP_P-LUC-TPsaD transformant, which were selected in example <3-2>, were divisionally cultured in several test tubes containing TAP liquid medium, the test tubes were dark-treated or exposed to light of 30 or 300 μmol photon/m²/s for 3 hours. Then, the transformants were harvested, the luciferase luminescence therefor was measured through Luminometer (GloMax™ 20/20; Promega, USA) using the *Renilla* Luciferase assay kit (E2810; Promega, USA) according to the protocol provided by the manufacturer. In order to analyze the level of the luciferase expression for each light intensity, the luminescence ratio, which was calculated by dividing the luminescence of the transformant irradiated with light of 300 μmol photon/m²/s by the luminescence of the transformant irradiated with light of 30 μmol photon/m²/s, was compared.

As a result, the luciferase reporter gene showed more stable and uniform expression pattern under 1LSIP_P of the present invention rather than under the cbr promoter derived from *Dunaliella bardawil* (table 3 and FIG. 6). That is, it was confirmed that the cbr promoter derived from *Dunaliella bardawil* exhibited a large deviation in promoter activity for each clone, but the 1LSIP_P promoter of the present invention exhibited a uniform level of promoter activity for each clone. In addition, the luciferase reporter gene exhibited a higher luminescence ratio under the cbr promoter derived from *Dunaliella bardawil* rater than under LSIP_P (4LSIP_P, 8LSIP_P, and 17LSIIP_P) derived from *Dunaliella* sp. (table 3 and FIG. 7). This means that LSIP_P derived from *Dunaliella* sp. is more sensitive to the light intensity than the cbr promoter derived from *Dunaliella bardawil* when regulating the luciferase expression.

It can be seen from the above results that LSIP_P of the present invention has, as a basic unit, 1LSIP_P having the nucleotide sequence of SEQ ID NO: 18, which exhibits more stable promoter activity than the cbr promoter derived from *Dunaliella bardawil*, and is more dependent on the light intensity than the cbr promoter derived from *Dunaliella bardawil* and thus regulates the expression of the gene linked to the downstream thereof in a light intensity-dependent manner.

TABLE 3

| | | Luminescence | | | | Luminescence ratio (light/dark) | | |
|---|---|---|---|---|---|---|---|---|
| Clone | | Light intensity (μmol photons/m$^2$/s) | | | | | | |
| | ID | 0 | 30 | 300 | 600 | 30 | 300 | 600 |
| Bar-CBR_P | 2 | 3104 | 1443 | 5682 | 4147 | 0.46 | 1.83 | 1.34 |
| | 3 | 39057 | 18840 | 215677 | 181575 | 0.48 | 5.52 | 4.65 |
| | 24 | 173306 | 386508 | 2177840 | 2951550 | 2.23 | 12.57 | 17.03 |
| | 32 | 497853 | 418948 | 9686064 | 4408146 | 0.84 | 19.46 | 8.85 |

As described above, preferable embodiments of the present invention has been exemplified, but the scope of the present invention is not limited to the above particular embodiments, and thus appropriate variations and modifications are possible within the range of claims of the present invention by any person skilled in the art.

The invention claimed is:

1. A light-inducible promoter comprising the nucleotide sequence of SEQ ID NO: 12.

2. The light-inducible promoter of claim 1, wherein the promoter comprises the nucleotide sequence of SEQ ID NO: 1.

3. The light-inducible promoter of claim 1, wherein the promoter comprises the nucleotide sequence of SEQ ID NO: 2.

4. An expression vector comprising the light-inducible promoter of claim 1.

5. The expression vector of claim 4, further comprising a multiple cloning site (MCS) for allowing a nucleotide sequence coding an exogenous protein to be operably inserted into the promoter.

6. A transformant transformed with the expression vector of claim 4.

7. An expression construct comprising a nucleotide sequence coding an exogenous protein and operably linked to a light-inducible promoter wherein the light-inducible promoter comprises the nucleotide sequence of SEQ ID NO: 12.

8. An expression vector comprising the expression construct of claim 7.

9. A transformant transformed with the expression vector of claim 8.

10. A method for producing an exogenous protein, the method comprising: (a) culturing the transformant of claim 9; and (b) irradiating the cultured transformant with light to produce the exogenous protein.

* * * * *

SEQUENCE LISTING

<160> NUMBER OF SEQ ID NOS: 21

<210> SEQ ID NO 1
<211> LENGTH: 845
<212> TYPE: DNA
<213> ORGANISM: Dunaliella sp.

<400> SEQUENCE: 1

```
tgcagcatta ccgctgactc agctcgacat atggtgttgg taattcagca caattgggct    60
caacaaagtt tttgctgtca gtgagagggc cgtagacgtc tacactcata catacacacg   120
tcgacaggag tgtagatggg agtgtgtgtg tgtaagtgtg tgcgtgcacg cgcgtatatg   180
catgtgtata tacgtgtttg cgtatatatg tgtgtgtgtg tatgtgtgtg tgttcatatg   240
tatgttgtgt tcatgcgtgc tgagaacgcg tgttcatgca cacctgtagc ctgtgcaccg   300
ttagcattct ggaaatgtct tttccagcct ctgagcacac ctcttggatc ctgttgtgtc   360
tgtgccccct ggatccttta ttaccctcga gggtagagct ctggatccca gtgtaggtgt   420
ctttgctagt gtactcctac acgtcctcaa tgcacgagcg tgcacactaa acacttgtgc   480
atgcactgtc accaggcttt ggcagcgcca ggaggttctt aaagtgacat ccgtgtcccg   540
cagcaactta cattgaccaa cagtcaacac cctccaaccc tcacaggttc aagacacata   600
caacactgtt cactcactcg tgatttgcaa aatgtaaagc cttggccctc ttggcttttt   660
ttttctcacg ggcagctcac ccaccgactc actcacgcac tcaccaacag agcgtggcct   720
cggagcgtga gggctccggg ccacacattt gccagcctga aaacttgcca aaaaccactc   780
atcatcaaaa caacaaaagc ttcaatcaaa actcgttcct acacccacac gaaccgaccc   840
gaaca                                                              845
```

<210> SEQ ID NO 2
<211> LENGTH: 1702
<212> TYPE: DNA
<213> ORGANISM: Dunaliella sp.

<400> SEQUENCE: 2

```
atggggccaa tcttgtgcag ttggatgcgg gcaacacaga ccgtttggcc cagcacaacc    60
tgcaagtccc tgagcaagtc tctaatcgtg ctgtaccttc caacctcttc aaacccacgg   120
tttcggtgca atccagacga aactccagcc gccctgatgc aatcttggtc actcctcacc   180
caactaaccc aaacagacca cccacttcac cctcataccg agtactgcgc agtatgggga   240
gtaccacaac tccagcccgt catattcact tgatagaaat caaatactgc aaagatacga   300
```

-continued

```
ggcctggtgc ccagctagaa gcctcacagc aacaacacag tgaactttgc aaacaactcc    360
aaggtgcaga gatcactatc cacccaatcc tcctgggtgt gggtgggact atctacactg    420
cccatacect tgatcaatta aaaaaaatag ggattgactc acagagatct gaaacacttg    480
caagaaaaat ccatgcccat tctgtacaat ttgcgcacaa acctacctct accagacgtg    540
ccattgaaaa taaaaacact catcatgaca ctggtgccct ggagcagcgt gctgccagaa    600
acccacctga tccacattca ctcccctctc atcttctggt gggggagact cacggctctt    660
tgagccaatg tgtctctctt tccttaattg atgtagggag agttttctct gcccacatag    720
tttttttctct tctttttctt ttctagctcc ttacctattt ggtggaaaga gctgagacct    780
ttcgaagcaa tgagtgtacg taatatggaa tcataccttt caaagggagc tagaggaacc    840
agtcgcctat tgccccatgc agcattaccg ctgactcagc tcgacatatg gtgttggtaa    900
ttcagcacaa ttgggctcaa caaagttttt gctgtcagtg agagggccgt agacgtctac    960
actcatacat acacacgtcg acaggagtgt agatgggagt gtgtgtgtgt aagtgtgtgc   1020
gtgcacgcgc gtatatgcat gtgtatatac gtgtttgcgt atatatgtgt gtgtgtgtat   1080
gtgtgtgtgt tcatatgtat gttgtgttca tgcgtgctga gaacgcgtgt tcatgcacac   1140
ctgtagcctg tgcaccgtta gcattctgga aatgtctttt ccagcctctg agcacacctc   1200
ttggatcctg ttgtgtctgt gcccctgga tcctttatta ccctcgaggg tagagctctg     1260
gatcccagtg taggtgtctt tgctagtgta ctcctacacg tcctcaatgc acgagcgtgc   1320
acactaaaca cttgtgcatg cactgtcacc aggctttggc agcgccagga ggttcttaaa   1380
gtgacatccg tgtcccgcag caacttacat tgaccaacag tcaacaccct caaccctca    1440
caggttcaag acacatacaa cactgttcac tcactcgtga tttgcaaaat gtaaagcctt   1500
ggccctcttg ctttttttt tctcacgggc agctcaccca ccgactcact cacgcactca    1560
ccaacagagc gtggcctcgg agcgtgaggg ctccgggcca cacatttgcc agcctgaaaa   1620
cttgccaaaa accactcatc atcaaaacaa caaaagcttc aatcaaaact cgttcctaca   1680
cccacacgaa ccgacccgaa ca                                            1702
```

<210> SEQ ID NO 3
<211> LENGTH: 183
<212> TYPE: PRT
<213> ORGANISM: Dunaliella sp.

<400> SEQUENCE: 3

```
Met Gln Leu His Met Asn Leu Ser Ala Ser Arg Ile Ala Ala Gly Ala
1               5                   10                  15

Ile Asn Val Arg Pro Ala Pro Phe Val Arg Gly Ala Ala Ala Pro Lys
            20                  25                  30

Arg Thr Ser Arg His Ile Val Arg Ala Glu Asn Asp Pro Ser Thr Pro
        35                  40                  45

Pro Pro Pro Gln Gly Ser Gln Glu Ser Pro Ser Ser Pro Ser Pro
    50                  55                  60

Pro Pro Pro Pro Gln Pro Thr Ala Ala Pro Thr Val Thr Glu
65                  70                  75                  80

Val Met Gly Phe Ser Gly Ala Pro Glu Ile Ile Asn Gly Arg Leu Ala
                85                  90                  95

Met Leu Gly Phe Val Ala Ala Leu Gly Ala Glu Leu Ser Thr Gly Glu
            100                 105                 110

Ser Val Leu Thr Gln Leu Ala Asp Glu Pro Thr Leu Ile Ala Leu Thr
        115                 120                 125
```

Phe Val Leu Phe Ser Ala Ala Ser Leu Val Pro Ala Phe Ala Arg Arg
            130                 135                 140

Lys Ser Asp Pro Val Gly Pro Phe Thr Pro Gln Ala Glu Met Thr Asn
145                 150                 155                 160

Gly Arg Ala Ala Met Ile Gly Phe Ala Ala Met Leu Val Tyr Glu Gly
                165                 170                 175

Val Gln Gly Ile Ala Leu Phe
            180

<210> SEQ ID NO 4
<211> LENGTH: 2084
<212> TYPE: DNA
<213> ORGANISM: Dunaliella sp.

<400> SEQUENCE: 4

| | | | | |
|---|---|---|---|---|
| cccgggctgg | taaaatccca | tatgcatgct | aaacacaagc | tgggctatgc | tgacaggaag |    60 |
| acaggctact | atacttacta | ccagagcttg | ctacctcacg | taaacaagaa | aattagcaat |   120 |
| gcctttggga | acatgcccgg | tctctcaact | cgaatgaaac | gcactgtctt | ccaatacagc |   180 |
| acaggcaccc | tctacaatca | gaaacatgcg | gtccgatata | aaagatccac | tagcctgaca |   240 |
| tgcccctac  | ctgattgcca | tcacatgggt | agcgctctcc | acatcctatc | tggctgccaa |   300 |
| tgtcctgtca | tgcgtaacat | ggtaactgaa | cgtcacaata | tcgcttgcag | gatgattttg |   360 |
| aaactggtca | gtgaaggctc | atatggggcc | aatcttgtgc | agttggatgc | gggcaacaca |   420 |
| gaccgtttgg | cccagcacaa | cctgcaagtc | cctgagcaag | tctctaatcg | tgctgtacct |   480 |
| tccaacctct | tcaaacccac | ggtttcggtg | caatccagac | gaaactccag | ccgccctgat |   540 |
| gcaatcttgg | tcactcctca | cccaactaac | ccaaacagac | cacccacttc | accctcatac |   600 |
| cgagtactgc | gcagtatggg | gagtaccaca | actccagccc | gtcatattca | cttgatagaa |   660 |
| atcaaatact | gcaaagatac | gaggcctggt | gcccagctag | aagcctcaca | gcaacaacac |   720 |
| agtgaacttt | gcaaacaact | ccaaggtgca | gagatcacta | tccacccaat | cctcctgggt |   780 |
| gtgggtggga | ctatctacac | tgcccatacc | cttgatcaat | taaaaaaaat | agggattgac |   840 |
| tcacagagat | ctgaaacact | tgcaagaaaa | atccatgccc | attctgtaca | atttgcgcac |   900 |
| aaacctacct | ctaccagacg | tgccattgaa | aataaaaaca | ctcatcatga | cactggtgcc |   960 |
| ctggagcagc | gtgctgccag | aaacccacct | gatccacatt | cactccctc  | tcatcttctg |  1020 |
| gtgggggaga | ctcacggctc | tttgagccaa | tgtgtctctc | tttccttaat | tgatgtaggg |  1080 |
| agagtttct  | ctgcccacat | agttttttct | cttcttttc  | ttttctagct | ccttacctat |  1140 |
| ttggtggaaa | gagctgagac | ctttcgaagc | aatgagtgta | cgtaatatgg | aatcatacct |  1200 |
| tacaaaggga | gctagaggaa | ccagtcgcct | attgccccat | gcagcattac | cgctgactca |  1260 |
| gctcgacata | tggtgttggt | aattcagcac | aattgggctc | aacaaagttt | tgctgtcag  |  1320 |
| tgagagggcc | gtagacgtct | acactcatac | atacacacgt | cgacaggagt | gtagatggga |  1380 |
| gtgtgtgtgt | gtaagtgtgt | gcgtgcacgc | gcgtatatgc | atgtgtatat | acgtgtttgc |  1440 |
| gtatatatgt | gtgtgtgtgt | atgtgtgtgt | gttcatatgt | atgttgtgtt | catgcgtgct |  1500 |
| gagaacgcgt | gttcatgcac | acctgtagcc | tgtgcaccgt | tagcattctg | gaaatgtctt |  1560 |
| ttccagcctc | tgagcacacc | tcttggatcc | tgttgtgtct | gtgcccctg  | gatcctttat |  1620 |
| taccctcgag | ggtagagctc | tggatcccag | tgtaggtgtc | tttgctagtg | tactcctaca |  1680 |
| cgtcctcaat | gcacgagcgt | gcacactaaa | cacttgtgca | tgcactgtca | ccaggctttg |  1740 |

| | |
|---|---|
| gcagcgccag gaggttctta aagtgacatc cgtgtcccgc agcaacttac attgaccaac | 1800 |
| agtcaacacc ctccaaccct cacaggttca agacacatac aacactgttc actcactcgt | 1860 |
| gatttgcaaa atgtaaagcc ttggccctct tggcttttt tttctcacgg gcagctcacc | 1920 |
| caccgactca ctcacgcact caccaacaga gcgtggcctc ggagcgtgag ggctccgggc | 1980 |
| cacacatttg ccagcctgaa aacttgccaa aaaccactca tcatcaaaac aacaaaagct | 2040 |
| tcaatcaaaa ctcgttccta cacccacacg aaccgacccg aaca | 2084 |

<210> SEQ ID NO 5
<211> LENGTH: 2418
<212> TYPE: DNA
<213> ORGANISM: Dunaliella sp.

<400> SEQUENCE: 5

| | |
|---|---|
| cccgggctgg taaaatccca tatgcatgct aaacacaagc tgggctatgc tgacaggaag | 60 |
| acaggctact atacttacta ccagagcttg ctacctcacg taaacaagaa aattagcaat | 120 |
| gccttttgga acatgcccgg tctctcaact cgaatgaaac gcactgtctt ccaatacagc | 180 |
| acaggcaccc tctacaatca gaaacatgcg gtccgatata aagatccac tagcctgaca | 240 |
| tgcccctac ctgattgcca tcacatgggg agcgctctcc acatcctatc tggctgccaa | 300 |
| tgtcctgtca tgcgtaacat ggtaactgaa cgtcacaata tcgcttgcag gatgattttg | 360 |
| aaactggtca gtgaaggctc atatggggcc aatcttgtgc agttggatgc gggcaacaca | 420 |
| gaccgtttgg cccagcacaa cctgcaagtc cctgagcaag tctctaatcg tgctgtacct | 480 |
| tccaacctct tcaaacccac ggtttcggtg caatccagac gaaactccag ccgccctgat | 540 |
| gcaatcttgg tcactcctca cccaactaac caaacagac cacccacttc accctcatac | 600 |
| cgagtactgc gcagtatggg gagtaccaca actccagccc gtcatattca cttgatagaa | 660 |
| atcaaatact gcaaagatac gaggcctggt gcccagctag aagcctcaca gcaacaacac | 720 |
| agtgaacttt gcaaacaact ccaaggtgca gagatcacta tccacccaat cctcctgggt | 780 |
| gtgggtggga ctatctacac tgcccatacc cttgatcaat taaaaaaat agggattgac | 840 |
| tcacagagat ctgaaacact tgcaagaaaa atccatgccc attctgtaca atttgcgcac | 900 |
| aaacctacct ctaccagacg tgccattgaa aataaaaaca ctcatcatga cactggtgcc | 960 |
| ctggagcagc gtgctgccag aaacccacct gatccacatt cactcccctc tcatcttctg | 1020 |
| gtgggggaga ctcacggctc tttgagccaa tgtgtctctc tttccttaat tgatgtaggg | 1080 |
| agagttttct ctgcccacat agttttttct cttctttttc ttttctagct ccttacctat | 1140 |
| ttggtggaaa gagctgagac ctttcgaagc aatgagtgta cgtaatatgg aatcatacct | 1200 |
| tacaaaggga gctagaggaa ccagtcgcct attgccccat gcagcattac cgctgactca | 1260 |
| gctcgacata tggtgttggt aattcagcac aattgggctc aacaaagttt ttgctgtcag | 1320 |
| tgagagggcc gtagacgtct acactcatac atacacacgt cgacaggagt gtagatggga | 1380 |
| gtgtgtgtgt gtaagtgtgt gcgtgcacgc gcgtatatgc atgtgtatat acgtgtttgc | 1440 |
| gtatatatgt gtgtgtgtgt atgtgtgtgt gttcatatgt atgttgtgtt catgcgtgct | 1500 |
| gagaacgcgt gttcatgcac acctgtagcc tgtgcaccgt tagcattctg gaaatgtctt | 1560 |
| ttccagcctc tgagcacacc tcttggatcc tgttgtgtct gtgcccctg gatcctttat | 1620 |
| taccctcgag ggtagagctc tggatcccag tgtaggtgtc tttgctagtg tactcctaca | 1680 |
| cgtcctcaat gcacgagcgt gcacactaaa cacttgtgca tgcactgtca ccaggctttg | 1740 |
| gcagcgccag gaggttctta aagtgacatc cgtgtcccgc agcaacttac attgaccaac | 1800 | agtcaacacc ctccaaccct cacaggttca agacacatac aacactgttc actcactcgt    1860 gatttgcaaa atgtaaagcc ttggccctct tggcttttt tttctcacgg gcagctcacc    1920 caccgactca ctcacgcact caccaacaga gcgtggcctc ggagcgtgag ggctccgggc    1980 cacacatttg ccagcctgaa aacttgccaa aaaccactca tcatcaaaac aacaaaagct    2040 tcaatcaaaa ctcgttccta cacccacacg aaccgacccg aacaatgcag ctgcacatga    2100 acctgtccgc ctcccggatc gcggccggtg ccatcaacgt gcgtcccgcg cccttcgtac    2160 gtggggctgc tacacccaag cgcacgagca ggcacatcgt gcgcgccgag aacgacccct    2220 ccactccccc tcccccacaa ggatcgcaag agtcccccag ctccagccct tccccacctc    2280 ctcctcctcc tcagccaaca gccgcagctc ctaccgtgac aggtgtgtaa aagctggccc    2340 caggaagttc cccctctgcc aggctggctg gttcttggga gtagtgtctg ctgaacttct    2400 gcatgcaatg tggtgcaa                                                 2418

<210> SEQ ID NO 6
<211> LENGTH: 27
<212> TYPE: DNA
<213> ORGANISM: Artificial Sequence
<220> FEATURE:
<223> OTHER INFORMATION: Gene Specific Primer 1

<400> SEQUENCE: 6
ttgcaccaca ttgcatgcag aagttca                                         27

<210> SEQ ID NO 7
<211> LENGTH: 20
<212> TYPE: DNA
<213> ORGANISM: Artificial Sequence
<220> FEATURE:
<223> OTHER INFORMATION: Gene Specific Primer 2

<400> SEQUENCE: 7
tgtaagttgc tgcgggacac                                                 20

<210> SEQ ID NO 8
<211> LENGTH: 9680
<212> TYPE: DNA
<213> ORGANISM: Artificial Sequence
<220> FEATURE:
<223> OTHER INFORMATION: Nucleotide Sequence of pN7-AR_P-LUC-PsaD

<400> SEQUENCE: 8
gtggcacttt tcggggaaat gtgcgcggaa cccctatttg tttatttttc taaatacatt      60
caaatatgta tccgctcatg agacaataac cctgataaat gcttcaataa tattgaaaaa     120
ggaagagtat gagtattcaa catttccgtg tcgcccttat tcccttttt gcggcatttt     180 gccttcctgt ttttgctcac ccagaaacgc tggtgaaagt aaaagatgct gaagatcagt     240
tgggtgcacg agtgggttac atcgaactgg atctcaacag cggtaagatc cttgagagtt     300
ttcgccccga agaacgtttt ccaatgatga gcacttttaa agttctgcta tgtggcgcgg     360
tattatcccg tattgacgcc gggcaagagc aactcggtcg ccgcatacac tattctcaga     420
atgacttggt tgagtactca ccagtcacag aaaagcatct tacggatggc atgacagtaa     480
gagaattatg cagtgctgcc ataaccatga gtgataacac tgcggccaac ttacttctga     540
caacgatcgg aggaccgaag gagctaaccg cttttttgca caacatgggg gatcatgtaa     600
ctcgccttga tcgttgggaa ccggagctga atgaagccat accaaacgac gagcgtgaca     660

```
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca gtttactcat atatacttt    1020
agattgattt aaaacttcat ttttaattta aaaggatcta ggtgaagatc cttttgata    1080
atctcatgac caaaatccct taacgtgagt tttcgttcca ctgagcgtca gaccccgtag    1140
aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt    1260
ttccgaaggt aactggcttc agcagagcgc agataccaaa tactgtcctt ctagtgtagc    1320
cgtagttagg ccaccacttc aagaactctg tagcaccgcc tacatacctc gctctgctaa    1380
tcctgttacc agtggctgct gccagtggcg ataagtcgtg tcttaccggg ttggactcaa    1440
gacgatagtt accggataag gcgcagcggt cgggctgaac ggggggttcg tgcacacagc    1500
ccagcttgga gcgaacgacc tacaccgaac tgagatacct acagcgtgag ctatgagaaa    1560
gcgccacgct tcccgaaggg agaaaggcgg acaggtatcc ggtaagcgg agggtcggaa    1620
caggagagcg cacgagggag cttccagggg gaaacgcctg gtatctttat agtcctgtcg    1680
ggtttcgcca cctctgactt gagcgtcgat ttttgtgatg ctcgtcaggg gggcggagcc    1740
tatgaaaaaa cgccagcaac gcggcctttt tacggttcct ggccttttgc tggccttttg    1800
ctcacatgtt ctttcctgcg ttatcccctg attctgtgga taaccgtatt accgcctttg    1860
agtgagctga taccgctcgc cgcagccgaa cgaccgagcg cagcgagtca gtgagcgagg    1920
aagcggaaga gcgcccaata cgcaaaccgc ctctccccgc gcgttggccg attcattaat    1980
gcagctggca cgacaggttt cccgactgga aagcgggcag tgagcgcaac gcaattaatg    2040
tgagttagct cactcattag gcaccccagg ctttacactt tatgcttccg gctcgtatgt    2100
tgtgtggaat tgtgagcgga taacaatttc acacaggaaa cagctatgac catgattacg    2160
ccaagcgcgc aattaaccct cactaaaggg aacaaaagct ggagctcgcc ggggatcga    2220
tcctctaggc cttctgctag tcagctgtga acagtaagt ttactcaaca cacggaaat    2280
gttagaaata aggtaattat gggaaattcg ccgaggaaga aaccgcggac catgcatgaa    2340
tacagactgc acaacgtctt tgtgttcatt actgcagggc gcatacacaa ttgccgctca    2400
cgcttgattt attgctggtt cttaaaacgc atgcgcttca agcgcaacag ctctacaaac    2460
cattgctgcg gtccctgtcg attctgcgct gttggcctga aggaatgcgc ctattcgcaa    2520
acacgcgtgg atgcgcaagc gcgacacatg aacggagccg atgcattctt gtcggctcga    2580
cgcggtttat tggtggtggc gctcctcgcg ttgcgcacca atcgtcactg gagcagtcga    2640
agccttgctt aatttcgcgg cgcggcaggc caggcttca actggtatgt tattaagcat    2700
gaacggccgt gcgggactgg accggctaac gtccctagag ccggccgctg aacatccaga    2760
atgtttggga gctggctggg agcaccactc gcagtgacat aatgcttgtc aattaagaag    2820
cggtgtcctg caggctgcgg tccaagcgag cgctgcgggc gacacggcac aggttgccac    2880
gcccagcact ggtgcgccag gcgccgagtg gctgcctgcc tcctggagg cgcagctggc    2940
gcccatcacg tcgcgcctg acgccaagga ggccctcagg caagtgtgaa gtgcggctgg    3000
cggcgtggcg cgttgccgcc cgcacaccag cggagcaggg cgcgcgcggt gtgcatgagg    3060
```

```
ggtgcagcgg ggtcgctgtt tggccgctac gtctgttgct gcggggatgc ggggcggtgc    3120
cgccggagcc tagggtgccc ctgcggcagg tgacacagac agggggggta gctgtcgcgg    3180
cagctcaggg gtgtgtgtgg cgagacctgc ccgcccgcag ttggcccgcc ctcatcaccc    3240
tggtgccgcc tgcccccgg cctgactgcc ccccgctgc cctcctgctg cccaccccac    3300 cccacccct gcacgccctc gcacacgccc ctcccaggcg gctgctggac gcgggcagtg    3360
gcctggcccc gctgccggcc gccgcccgca ccgcctccaa ccgggtcatg gctgcacgg    3420 cgcaggtgtg gctggcggct gagacggacg cggccggccg catggccttc caggtgggcc    3480
gggcgggcgg gcgggaggcg gccgtgggcg ctgtgggcag acggaggggg gaggcggggg    3540
gaggaggcgg ggagttgcat ggtgggtctg tgtgcaagtg accagagctg aaccggagat    3600
gtgataccgg ggggtggggt gtgttgtggg gtcgccggg ctggctgtcc cggcccgggt    3660
gcaggtgggg gcgggtgagg ccggaggcga ggtggagggc aacacggagc ggctgcagac    3720 ctgtgggcg ctggtgggcg gcagcggacc gctcgctgac cgccctcggg ccgaacccac    3780
ccagctcgga aggggcgagc ctgcacgaca ccgcacgggc gctgcgtgcg gctggtccgg    3840
acaggggact ggacggagga cgcacggcg catgtgcacg tgtgtcagtg acgcagcacg    3900
tgcaagggca ccgcacacac caggcgctgc cggctggggc gcgtaccata caccccaacg    3960
cgtcggttct gggtcctatt ccattgggct cgggcatgtg accccaacgc gccactccgc    4020
acgtccacac gcgcagggct ggagcgacag tgaggtcagt cgcgggctgg tggcgctgct    4080
ggtgcgcggg ctgagcggct gcacgcccga ggaggtcatg caggtgtgtg tgcgtgcgca    4140
gagagcacaa gaaggaagga aacaggaatg actgtgcgtg tgcatagatc cggattcgtg    4200
ccttgcgttt gggcgtgtga gggatagggc tcaagggctg acaggtgttg ggggcggct    4260 gagggctgcg ctaccctgc agctgtgcag cgacacacgc cgcgacccgc accctcccc    4320 ccctccccc caggtgtcgg cgagccaggt gcagcagcgg ctgtcgcggg tgctggggcg    4380
ctccgtgctg ccgccgggcc gcgccaacgg actgggcaac atgctggaga gcgcgcgcaa    4440
gcgggcggcg ctggcggcgg cggcggcggc cgggcggcgg ctggacgtgt tccctcgct    4500 gctcatcacc gcagacgccc tcacgccgca ggtactcggg gcgcgggtgca ctggggctag    4560 gaactgggcg cctggggggg tagccatcca tgggatggtg tgtatcctgg gggggaggg    4620 aaagggtgat tgtccatgaa agaccgaagg accaaagccc atcccgagtt actcgaggcc    4680 gggggtatg tgggggtgg gcggactggg ggtgtgttgg tgggcgacca cgacacacgc    4740 gccgacccg caccccgccg ccctgactgg cgctggcgcc tgcggggccg ctgtgcaggg    4800
cgccttcgcg gaggcccagg cgcgctacct ggcgccggat gcggccgccc gcgacaagca    4860
catcggcgtg gtgcgcacat tctacatgga cccgcaggtg cagggcgtgt tgtcggctgc    4920
tgcggaggag tggccgcaca tcgccatcag tgactcgctg gtgatggcgg acacggccgt    4980
gcgcatggcg gaggcgggat gcaccaccat ctgtgtgctg ggtgtggact tcatgagtga    5040
gaacgtgcgc gccatcctgg atgaggcggg gcacagcgca gtgcaggtgt accggctggc    5100
tgagtcggac attggctgct cgctggccga ggcggcggag agcgactcct acagccgcta    5160
cctgcagcag gccgcacaca cacccaacag cgtgcacgtg gtgtacatca acacctcgct    5220
gcgcaccaag gcccgtgcgc acgcgcttgt gcccaccatc acctgcacct cctccaacgt    5280
ggtgcagacg tgtctggcgg cctttgcgga cgtgccgggc gccacggtgt ggtacgccc    5340 cgacacctac atgggcgcca acctggcgca gctgttcgcc gacctggcct cgggcgccgc    5400
```

-continued

```
cagcgacgac gacgtgcgcg cgctgcaccc cgcacacacg gtggacagca tcaggtctct    5460
gttgccgcgc ctgcgctact tcactgacgg cacgtgcatc gtgcaccaca tctttggcgg    5520
cgaggtgacg gagctggtgg ctgcgggcta cggcgacgcc tacctggccg cgcactttga    5580
ggtgccgggc gagatgttcc ggctggccat gcaggccaag cgctcccggg gcatgggtgt    5640
ggtgggctcc acctccaaca tcctggactt catcgcggac aagctgcgcg aggctctgtc    5700
cgcgccgcac ccggagcggc tgcagttcgt gctgggcacg gaggcgggca tgatcacgtc    5760
catagtgcgc aaggtgcagg ggctgctgcg ccagtcgggt cgtactgacg tggaggtgga    5820
ggtggtgttc ccggtggcgc cctccgccgt ggccacgccg cagcagaggc cgcaggaggg    5880
cgcggcgccg ctcacactgc ccaccgggct ggcgctggtg ccgggtcccg cctccggcga    5940
gggctgcagc ctggagggcg gctgcgcggc ctgcccctac atgaagatga cacccctggc    6000
cgcactggtg tccgtgtgcg agcgcgtggg cagcccagca ggcgaggcca gcctggagcg    6060
ctaccggccg cgcacctatg gcggcgagac agtgggcggc cgcagcctgg ccgccgccgg    6120
ctgtgtgccc atcctgcaca tgcgcaactt ccagcgcagc cagggccgcc gcctggggcc    6180
ggacctgctg caggacatcg ccagccgcca caccgcccgg taggggggcag gcggcggacc    6240
ggcggagccc aggggagggg ggcggcgcaa ggcgtggtgg ccatgcgctc gagtgggctg    6300
gatgcgcagg atgagagcgg tgggtgggga ggagcaccgc gtagttagcg agtgagcggg    6360
cgagtgagtg ggagagtgcg gaggattgga ggacatctgg tgtttgaagg tcaagagggc    6420
gcaaccgtac aatgctgcga ggggtaggga caatgtgact ggcgcccaag aggcggcgtg    6480
cgggcgcgcc ttgcctagcg ttgctcatta ttagcgggtc ctgggaggcg attgtgccca    6540
cattggtgac ggtagcggta gcggtggcat tggcaatggc ggtagcggtg caatggtgg     6600
tggcggtggt gcgtgttcac ccgcttgccc cgggacgcgc agtcccttgc gtgcaggctg    6660
cgtcggtagg gctggctggc aggttgggat ggtctaatgc gacaggttca gcgcgtggga    6720
gcaactggtt aagaagagaa caattgcaag acgtccgcca acatgggcgg gatgggtaac    6780
gcatggcaga ccatggagta ccgtgcgcca gccggcacag gtcaggaggg caggggggcgc    6840
ggggcttaac cggcgtgtaa ttgttggtca agcacataca taacacaccc acgcgcacgt    6900
cgtgtccact tgacacacct gaggtcaaag caaaaggaag atgctggcac agtgaagcca    6960
gccaacaacc agccatgtcc gagctccacc gcggtggcgg ccgcgctcta gaagcttgga    7020
agctctggaa gggccgcgat ggggcgcgcg cgtccagaa ggcgccatac ggcccgctgg     7080
cggcacccat ccggtataaa agcccgcgac cccgaacggt gacctccact ttcagcgaca    7140
aacgagcact tatacatacg cgactattct gccgctatac ataaccactc agctagctta    7200
agatcccatc aagcttgcat gccgggcgcg ccagaaggag cgcagccaaa ccaggatgat    7260
gtttgatggg gtatttgagc acttgcaacc cttatccgga agcccctgg cccacaaagg      7320
ctaggcgcca atgcaagcag ttcgcatgca gcccctggag cggtgccctc ctgataaacc    7380
ggccaggggg cctatgttct ttactttttt acaagagaag tcactcaacg gatccccgg     7440
gctgcaggaa ttcactagtg attcgatggc cagcaaggtg tacgaccccg agcagcgcaa    7500
gcgcatgatc accggccctc agtggtgggc tcgctgcaag cagatgaacg tgctggacag    7560
cttcatcaac tactacgaca gcgagaagca cgccgagaac gccgtgatct tcctgcacgg    7620
caacgccgcc agcagctacc tgtggcgcca cgtggtgccc cacatcgagc ccgtggcccg    7680
ctgcatcatc cccgacctga tcggcatggg caagagcggc aagagcggca acggcagcta    7740
ccgcctgctg gaccactaca gtacctgac cgcctggttc gagctgctga acctgcccaa    7800
```

| | |
|---|---|
| gaagatcatc ttcgtgggcc acgactgggg cgcctgcctg gccttccact acagctacga | 7860 |
| gcaccaggac aagatcaagg ccatcgtgca cgccgagagc gtggtggacg tgatcgagag | 7920 |
| ctgggacgag tggcccgaca tcgaggagga catcgccctg atcaagagcg aggagggcga | 7980 |
| gaagatggtg ctggagaaca acttcttcgt ggagaccatg ctgcccagca agatcatgcg | 8040 |
| caagctggag cccgaggagt tcgccgccta cctggagccc ttcaaggaga agggcgaggt | 8100 |
| gcgccgtccc accctgagct ggcctcgcga gatccccctg gtgaagggcg caagcccga | 8160 |
| cgtggtgcag atcgtgcgca actacaacgc ctacctgcgc gccagcgacg acctgcccaa | 8220 |
| gatgttcatc gagagcgacc ccggcttctt cagcaacgcc atcgtggagg cgccaagaa | 8280 |
| gttccccaac accgagttcg tgaaggtgaa gggcctgcac ttcagccagg aggacgctcc | 8340 |
| cgacgagatg ggcaagtaca tcaagagctt cgtggagcgc gtgctgaaga acgatacgta | 8400 |
| atcctggcag cagctggacc gcctgtacca tggagaagag ctttacttgc cgggatggcc | 8460 |
| gatttcgctg attgatacgg gatcggagct cggaggcttt cgcgctaggg gctaggcgaa | 8520 |
| gggcagtggt gaccagggtc ggtgtggggt cggcccacgg tcaattagcc acaggaggat | 8580 |
| caggggggagg taggcacgtc gacttggttt gcgaccccgc agttttggcg gacgtgctgt | 8640 |
| tgtagatgtt agcgtgtgcg tgagccagtg gccaacgtgc cacacccatt gagaagacca | 8700 |
| accaacttac tggcaatatc tgccaatgcc atactgcatg taatggccag gccatgtgag | 8760 |
| agtttgccgt gcctgcgcgc gccccggggg cggggggga cgggtggggg taggggggtc | 8820 |
| tcacgggaac agcacgctag gggtcagggg gggggggggg cgcagtttag ctgaccagcc | 8880 |
| gtgggatgat gcacgcattt gcaaggacag ggtaatcaca gcagcaacat ggtgggctta | 8940 |
| ggacagctgt gggtcagtgg acggacggca ggggagggac ggcgcggctc gggagacagg | 9000 |
| gggagacggc gtgactgtgc acatcggtca attcgcccta tagtgagtcg tattacgcgc | 9060 |
| gctcactggc cgtcgtttta caacgtcgtg actgggaaaa ccctggcgtt acccaactta | 9120 |
| atcgccttgc agcacatccc cctttcgcca gctggcgtaa tagcgaagag gcccgcaccg | 9180 |
| atcgcccttc ccaacagttg cgcagcctga atggcgaatg gacgcgccc tgtagcggcg | 9240 |
| cattaagcgc ggcgggtgtg gtggttacgc gcagcgtgac cgctacactt gccagcgccc | 9300 |
| tagcgcccgc tcctttcgct ttcttccctt cctttctcgc cacgttcgcc ggctttcccc | 9360 |
| gtcaagctct aaatcggggg ctcccttag ggttccgatt tagtgcttta cggcacctcg | 9420 |
| accccaaaaa acttgattag ggtgatggtt cacgtagtgg gccatcgccc tgatagacgg | 9480 |
| tttttcgccc tttgacgttg gagtccacgt tctttaatag tggactcttg ttccaaactg | 9540 |
| gaacaacact caaccctatc tcggtctatt cttttgattt ataagggatt ttgccgattt | 9600 |
| cggcctattg gttaaaaaat gagctgattt aacaaaaatt taacgcgaat tttaacaaaa | 9660 |
| tattaacgct tacaatttag | 9680 |

<210> SEQ ID NO 9
<211> LENGTH: 23
<212> TYPE: DNA
<213> ORGANISM: Artificial Sequence
<220> FEATURE:
<223> OTHER INFORMATION: Forward Primer for 8LSIP_P

<400> SEQUENCE: 9

| | |
|---|---|
| tctagatgca gcattaccgc tga | 23 |

<210> SEQ ID NO 10

```
<211> LENGTH: 24
<212> TYPE: DNA
<213> ORGANISM: Artificial Sequence
<220> FEATURE:
<223> OTHER INFORMATION: Forward Primer for 17LSIP_P

<400> SEQUENCE: 10
tctagaatgg ggccaatctt gtgc                                           24

<210> SEQ ID NO 11
<211> LENGTH: 24
<212> TYPE: DNA
<213> ORGANISM: Artificial Sequence
<220> FEATURE:
<223> OTHER INFORMATION: Reverse Primer for all LSIP_Ps

<400> SEQUENCE: 11
gaattctgtt cgggtcggtt cgtg                                           24

<210> SEQ ID NO 12
<211> LENGTH: 439
<212> TYPE: DNA
<213> ORGANISM: Dunaliella sp.

<400> SEQUENCE: 12
cccagtgtag gtgtctttgc tagtgtactc ctacacgtcc tcaatgcacg agcgtgcaca    60
ctaaacactt gtgcatgcac tgtcaccagg ctttggcagc gccaggaggt tcttaaagtg   120
acatccgtgt cccgcagcaa cttacattga ccaacagtca acaccctcca accctcacag   180
gttcaagaca catacaacac tgttcactca ctcgtgattt gcaaaatgta aagctttggc   240
cctcttggct tttttttttct cacgggcagc tcacccaccg actcactcac gcactcacca   300
acagagcgtg gcctcggagc gtgagggctc cgggccacac atttgccagc ctgaaaactt   360
gccaaaaacc actcatcatc aaaacaacaa aagcttcaat caaaactcgt tcctacaccc   420
acacgaaccg acccgaaca                                                439

<210> SEQ ID NO 13
<211> LENGTH: 17
<212> TYPE: DNA
<213> ORGANISM: Artificial Sequence
<220> FEATURE:
<223> OTHER INFORMATION: Forward primer for 1LSIP_P

<400> SEQUENCE: 13
cccagtgtag gtgtctt                                                   17

<210> SEQ ID NO 14
<211> LENGTH: 1198
<212> TYPE: DNA
<213> ORGANISM: Dunaliella bardawil
<220> FEATURE:
<221> NAME/KEY: promoter
<222> LOCATION: (25)..(1198)

<400> SEQUENCE: 14
ggcggcggag aaagggagaa gaagagtccg agtgtcccgg ggcatggcga gcaaccctcc    60
agatccccat tcgtcctgtt tctggctctc ttctaggcta gctacgtcta gtgtaggttc   120
tgaggcctcc tggtgaggcc tctagctctc caattaaaga accttccctt aatgcacgcg   180
gccttggctt gcgtaaactt ttggttttct tttctttgca agcaaaggga ggcattataa   240 tcatttttttt cttaatcaga cattcatgta gcacagacca acttggtgtt atccttccaa   300
```

| | |
|---|---|
| ctccaaggat atgcttcagt aaacacacat gcacaatctg cgatttagcc atctcagctg | 360 |
| agatggcctg cagctcctcg cacccacag ttgcagctcc tcgcacccca cagctgcagc | 420 |
| tccttgtacc ccacattcgg ctagcatgca tgcatgcagg aagaacatgt gccttagtca | 480 |
| gccttggcac ggtgtgaggc ctatccgcca gctgcctctg ctactgcgca cacatgtgaa | 540 |
| tgcaaacacc tgataatgga cagccttggc tcactaaacc tacttaaaaa gcaaatgttg | 600 |
| tattcaggca ataggcttcg gctcggggag tcctcaccca tgttagccgc ccagagaaaa | 660 |
| gctggtacac cctgtgtatg tgcgtgttgg catgcgccta tgccggcagt tcctgagcac | 720 |
| aaatgtgtgc tcgcatgaga ctgcgcagcc gcatgcagcc gcatgccttc cctcaattga | 780 |
| gtctcctcaa tccaccgaca cacaattaca catgtgac tcttacaggc ttgagtatct | 840 |
| gaatttccaa gcctactggt ctagggccc ctgcttgctt gctggtcaac tggcggtcaa | 900 |
| caccctccaa caacgccagt gtggcaacac cgtcatggag gccgtcgtgt tcacgtaagt | 960 |
| tgcaaaacaa acctgtgcaa attttgtggt actccttttc acagcaacgc actggttcac | 1020 |
| atttcgcact caaagctcca acaaagcgca aggttctcgg aatttgaggg ttctcggcca | 1080 |
| caagtttgcc accctcaaag gtggaaattc accaatgtag gatgaaaact aaatactatc | 1140 |
| caaacacttg tgcacccta ttccggcgta ggacgcttaa tcgatccgac caactacg | 1198 |

<210> SEQ ID NO 15
<211> LENGTH: 1626
<212> TYPE: DNA
<213> ORGANISM: Dunaliella bardawil
<220> FEATURE:
<221> NAME/KEY: promoter
<222> LOCATION: (25)..(1198)

<400> SEQUENCE: 15

| | |
|---|---|
| tgggagggga tttgctggac gcacggcggc ggagaaaggg agaagaagag tccgagtgtc | 60 |
| ccggggcatg gcgagcaacc ctccagatcc ccattcgtcc tgtttctggc tctcttctag | 120 |
| gctagctacg tctagtgtag gttctgaggc ctcctggtga ggcctctagc tctccaatta | 180 |
| aagaaccttc ccttaatgca cgcggccttg gcttgcgtaa actttggtt ttcttttctt | 240 |
| tgcaagcaaa gggaggcatt ataatcattt ttttcttaat cagacattca tgtagcacag | 300 |
| accaacttgg tgttatcctt ccaactccaa ggatatgctt cagtaaacac acatgcacaa | 360 |
| tctgcgattt agccatctca gctgagatgg cctgcagctc ctcgcacccc acagttgcag | 420 |
| ctcctcgcac cccacagctg cagctccttg taccccacat tcggctagca tgcatgcatg | 480 |
| caggaagaac atgtgcctta gtcagccttg gcacggtgtg aggcctatcc gccagctgcc | 540 |
| tctgctactg cgcacacatg tgaatgcaaa cacctgataa tggacagcct ggctcacta | 600 |
| aacctactta aaaagcaaat gttgtattca ggcataggc ttcggctcgg ggagtcctca | 660 |
| cccatgttag ccgcccagag aaaagctggt acaccctgtg tatgtgcgtg ttggcatgcg | 720 |
| cctatgccgg cagttcctga gcacaaatgt gtgctcgcat gagactgcgc agccgcatgc | 780 |
| agccgcatgc cttccctcaa ttgagtctcc tcaatccacc gacacacaca attacacatg | 840 |
| tgactcttac aggcttgagt atctgaattt ccaagcctac tggttctagg gcccctgctt | 900 |
| gcttgctggt caactggcgg tcaacaccct ccaacaacgc cagtgtggca acaccgtcat | 960 |
| ggaggccgtc gtgttcacgt aagttgcaaa acaaacctgt gcaaattttg tggtactcct | 1020 |
| tttcacagca acgcactggt tcacatttcg cactcaaagc tccaacaaag cgcaaggttc | 1080 |
| tcggaatttg agggttctcg gccacaagtt tgccacccct caaaggtggaa attcaccaat | 1140 |

-continued

```
gtaggatgaa aactaaatac tatccaaaca cttgtgcacc cttattccgg cgtaggacgc    1200
ttaatcgatc cgaccaacta cgatgcagct gcacatgaac ctgcccacct cccgcatcgc    1260
ggccggtgct tccatcaatg ttcgtcccgc acctctcttg cgtactgctg cacccaagcg    1320
cgtgtgcaag catatcgtgc gggcggagaa caacccctcc actcccctc catctagccc     1380 ttcccctccc cctcccccto ccactcctgc tgccccgact gtgacaggtg tgagaaagct    1440
gtagccatcc tgaagcacct cccatgctgg ctcatgtgaa cttcatcttt gtgaacctcc    1500
ctgagtgttt taaactgttg aagctaacac acactcgcac acatacacac acacacacac    1560
acacacacac acacacacac acacacacac acacacacac acacacacac acacacacac    1620
acacac                                                               1626

<210> SEQ ID NO 16
<211> LENGTH: 26
<212> TYPE: DNA
<213> ORGANISM: Artificial Sequence
<220> FEATURE:
<223> OTHER INFORMATION: Forward primer for Bar-CBR_P

<400> SEQUENCE: 16
tctagaggcg gcggagaaag ggagaa                                         26

<210> SEQ ID NO 17
<211> LENGTH: 30
<212> TYPE: DNA
<213> ORGANISM: Artificial Sequence
<220> FEATURE:
<223> OTHER INFORMATION: Reverse primer for Bar-CBR_P

<400> SEQUENCE: 17
gaattccgta gttggtcgga tcgattaagc                                     30

<210> SEQ ID NO 18
<211> LENGTH: 100
<212> TYPE: DNA
<213> ORGANISM: Dunaliella sp.

<400> SEQUENCE: 18
catttgccag cctgaaaact tgccaaaaac cactcatcat caaaacaaca aaagcttcaa    60
tcaaaactcg ttcctacacc cacacgaacc gacccgaaca                          100

<210> SEQ ID NO 19
<211> LENGTH: 17
<212> TYPE: DNA
<213> ORGANISM: Artificial Sequence
<220> FEATURE:
<223> OTHER INFORMATION: Forward primer for 1LSIP_P

<400> SEQUENCE: 19
catttgccag cctgaaa                                                   17

<210> SEQ ID NO 20
<211> LENGTH: 15
<212> TYPE: DNA
<213> ORGANISM: Artificial Sequence
<220> FEATURE:
<223> OTHER INFORMATION: Forward primer for Luciferase

<400> SEQUENCE: 20
atggccagca aggtg                                                     15
```

```
<210> SEQ ID NO 21
<211> LENGTH: 19
<212> TYPE: DNA
<213> ORGANISM: Artificial Sequence
<220> FEATURE:
<223> OTHER INFORMATION: Reverse primer for Luciferase

<400> SEQUENCE: 21
ttacgtatcg ttcttcagc                                                 19
```